United States Patent [19]
Jondal

[11] Patent Number: 5,807,559
[45] Date of Patent: Sep. 15, 1998

[54] COMPOSITIONS FOR GENERATING T CELL IMMUNITY AGAINST CARBOHYDRATE STRUCTURES

[75] Inventor: Mikael Jondal, Stockholm, Sweden

[73] Assignee: Astra Aktiebolag, Sodertalje, Sweden

[21] Appl. No.: 54,860

[22] Filed: Apr. 27, 1993

[30] Foreign Application Priority Data

| Apr. 28, 1992 | [SE] | Sweden | 9201338 |
| Sep. 7, 1992 | [SE] | Sweden | 9202553 |
| Dec. 23, 1992 | [SE] | Sweden | 9203897 |
| Apr. 6, 1993 | [SE] | Sweden | 9301141 |

[51] Int. Cl.$^6$ .......................... A61K 39/00; A61K 31/70; A61K 45/05; A61K 47/00
[52] U.S. Cl. ................................. 424/278.1; 424/277.1; 424/174.1; 424/184.1; 530/403; 530/300; 530/402; 435/69.1; 514/8
[58] Field of Search ..................... 530/403, 300, 530/402; 435/69.1; 514/8, 174.1, 277.1; 424/278.1

[56] References Cited

U.S. PATENT DOCUMENTS

| 5,229,289 | 7/1993 | Kjeldsen et al. . |
| 5,334,379 | 8/1994 | Pillai et al. . |
| 5,389,530 | 2/1995 | Hakomori . |
| 5,500,215 | 3/1996 | Hakomori . |

FOREIGN PATENT DOCUMENTS

| 0427347 | 5/1991 | European Pat. Off. . |
| 0429816 | 6/1991 | European Pat. Off. . |
| 2004744 | 4/1979 | United Kingdom . |
| 8800053 | 1/1988 | WIPO . |
| 8906974 | 8/1989 | WIPO . |
| 8907448 | 8/1989 | WIPO . |
| 9103494 | 3/1991 | WIPO . |

OTHER PUBLICATIONS

Masazumi Matsumura et al., "Emerging Principles for the Recognition of Peptide Antigens by MHC Class I Molecules," Science, vol. 257, Aug. 1992, pp. 927–934.
Macharlan et al., "Stimulation of cytotoxic T–lymphocyte responses by rabies virus glycoprotein and identification fo an immunodominant domain," Mol Immunol 1986 Jul.; 23(7): 733–741.
O'Neill. 1991. Monoclonal Antibodies Which Identify Carbohydrate–Defined . . . Immunol & Cell Biol. 69:159–165.
Hertel–Wulff et al. 1983. Arsonate–Specific Murine T–Cell Clones. J. Exp. Med. 157:987–997.
Bjorkman et al. 1990. Structure, Function & Diversity of Class I Major . . . Ann. Rev. Biochem. 59:253–288.
Harding et al. PNAS, 88: 2740–2744, 1991.
Townsend et al, Ann. Rev. Immunol. 7: 601–24, 1989.
Townsend et al. J. Exp. Med. 168: 1211–1224, Oct. 1988.
Haurum et al, J Exp Med. 180: 739–744, Aug. 1994.
Harding et al., J. Immunol. 151: 2419–2425, 1993.
Abdel–Motal et al, Eur. J. Immunol 26: 544–551, 1996.
Wang et al, 1991. Tetrahedron Letters. 32(47):6827–30.
Hakomori 1991, Current Opin. Immunol. 3:646–653.
Bowie et al. 1990. Science 247: 1306–1310.
Pleskova et al. 1988. Neoplasma. 35(6): 657–664.
Houghten et al. 1986. Vaccines 86. 21–25.
Misra et al 1987. Immunogenetics. 26: 204–210.
Kumar et al. 1990. Amino Acid Variations at a Single Residue in an Autoimmune . . . , PNAS 87: 1337–1341.
Otvos et al., "Automated Solid–Phase Synthesis of Glycopeptides . . . ," Tetrahedron Letters, vol. 31, No. 41, pp. 5889–5892, 1990.
Elofsson et al., "Building Blocks for Glycopeptide Synthesis . . . ," Tetrahedron Letters, vol. 32, No. 51, pp. 7613–7616, 1991.
Uchiyama et al., "Synthesis of the 2', 3'–Dideoxynucleoside Derivatives," Chem. Pharm.Bull., 39 (11) 3091–3093 (1991).
Elliott et al., "Naturally processed peptides," Nature, vol. 348, pp. 195–197 (15 Nov. 1990).
Henningsson et al., "T Cell recognition of a tumor–associated glycoprotein . . . , " Cancer Immunol Immunother (1987) 25:231–241.
Ortmann et al., "Synthetic Peptides Anchor T Cell–Specific TND Epitopes to MHC," The Journal of Immunology, vol. 148, 1445–1450, No. 5, Mar. 1, 1992.
Rotzschke and Falk, "Naturally–occurring peptide antigens . . . ," Immunology Today, vol. 12, No. 12, 1991, pp. 447–455.
Tsomides and Eisen, "Antigenic Structures Recognized by Cytotoxic T Lymphocytes," The Journal of Biological Chemistry, vol. 266, No. 6, pp. 3357–3360 (Feb. 25, 1991).
Jardetzky et al., "Identification of self peptides bound to purified HLA–B27," Nature, vol. 353, pp. 326–329 (Sep. 26, 1991).
Bouillot et al., "Physical association between MHC class 1 molecules and immunogenic peptides," Nature, vol. 339, pp. 473–475 (Jun. 8, 1989).
Dialog Accession No. 07932964, "Monoclonal antibodies which identify carbohydrate–defined MHC epitopes" (Abstract from Database) Immunol. Cell. Biol., Jun. 1991, 69 (Pt 3) pp. 159–165.
Ishioka et al., "MHC Interaction and T. Cell Recognition . . . ," (Abstract from Database), J. Immunol., 148(8):2446–51 (Apr. 15, 1992).
Pimlott et al., "Glycopeptides inhibit [cell specific] cytotoxic T lymphocyte recognition . . . ," (Abstract from Database) J. Immunol., 136(1), 6–11 (Jan. 1986).

Primary Examiner—Nita Minnifield
Attorney, Agent, or Firm—White & Case L.L.P.

[57] ABSTRACT

The present invention relates to a novel class of immunologically active compounds, to processes for their production and to their use in therapy. In particular, the invention provides immunogenic peptide-carbohydrate conjugates useful for generating T cell immunity against tumor-associated carbohydrate structures, or against carbohydrate structures expressed on infectious agents and/or infected host cells. The immunogenic conjugate comprises a peptide component capable of binding a MHC class I molecule and a carbohydrate component having the same immunogenic characteristics of the carbohydrate structure on the tumor cell, infectious agent or the infected cells.

12 Claims, 13 Drawing Sheets

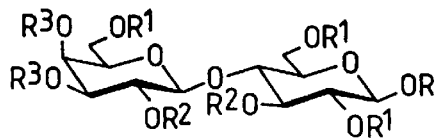

1: R=CH₂CH₂Si(CH₃)₃; R¹,R²,R³=Ac
2: R=CH₂CH₂Si(CH₃)₃; R¹,R²,R³=H
4: R=CH₂CH₂Si(CH₃)₃; R¹,R²=Bzl; R³=H
10: R=CH₂CH₂Br; R¹,R²,R³=Ac
11: R=CH₂CH₂Br; R¹,R²,R³=H
13: R=CH₂CH₂Br; R¹=Bz; R²,R³=H

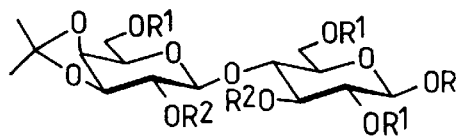

3: R=CH₂CH₂Si(CH₃)₃; R¹,R²=Bzl
12: R=CH₂CH₂Br; R¹,R²=H

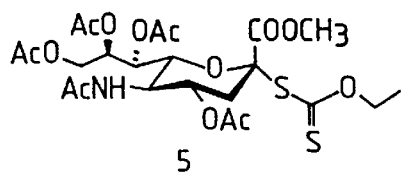

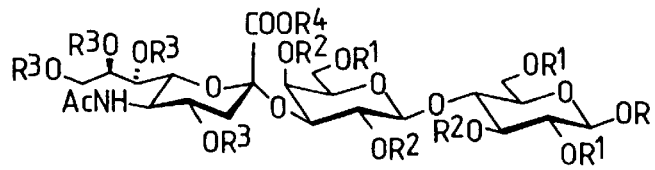

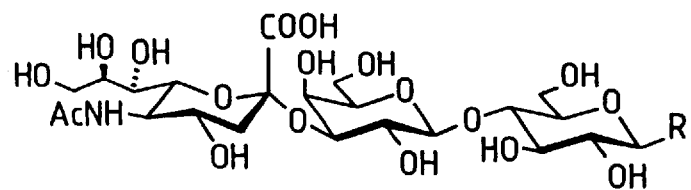
21: R= 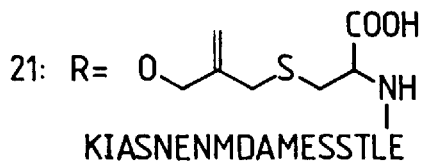
KIASNENMDAMESSTLE
22: R= 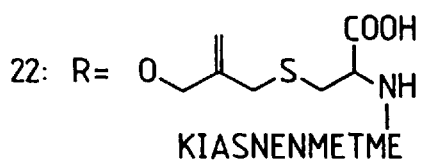
KIASNENMETME
23: R= 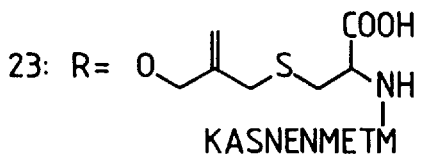
KASNENMETM
24: R= 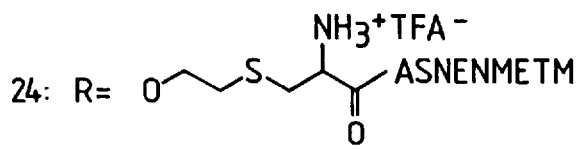
ASNENMETM
25: R= 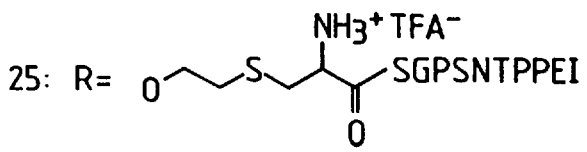
SGPSNTPPEI
FIG. 2

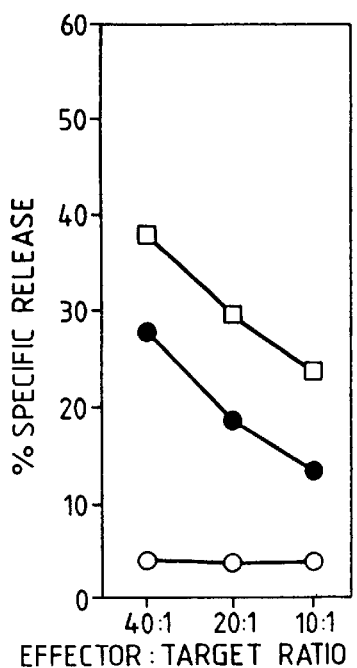 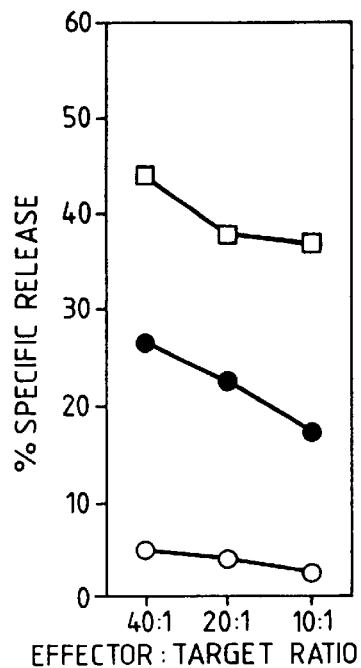 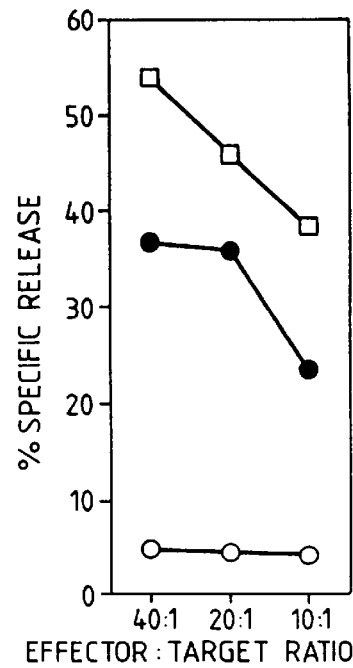
FIG. 3A  FIG. 3B  FIG. 3C
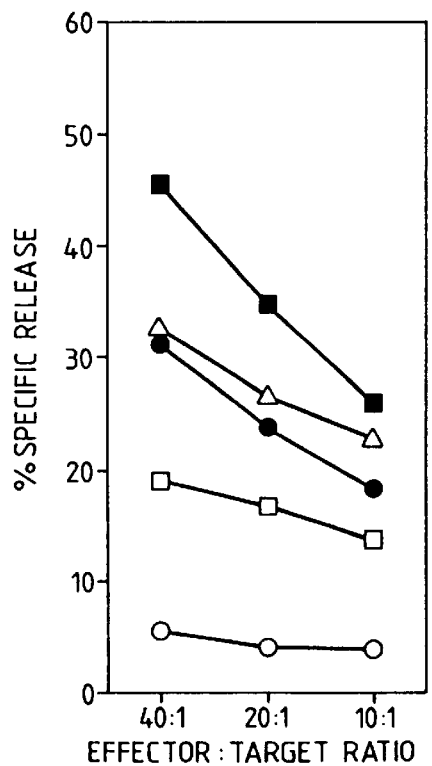 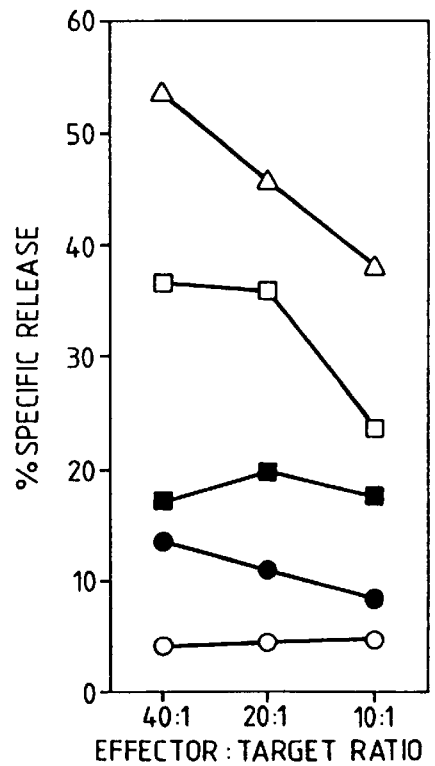
FIG. 4A  FIG. 4B

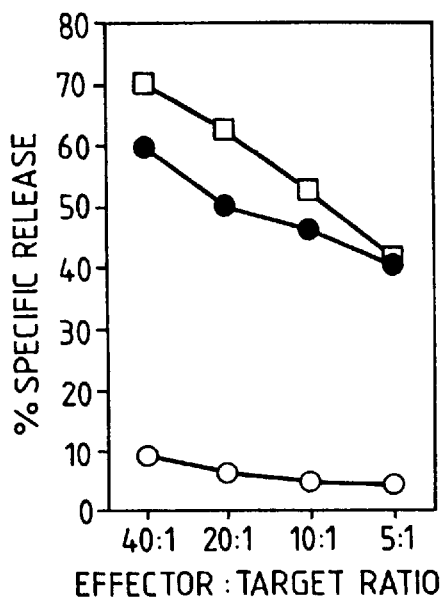 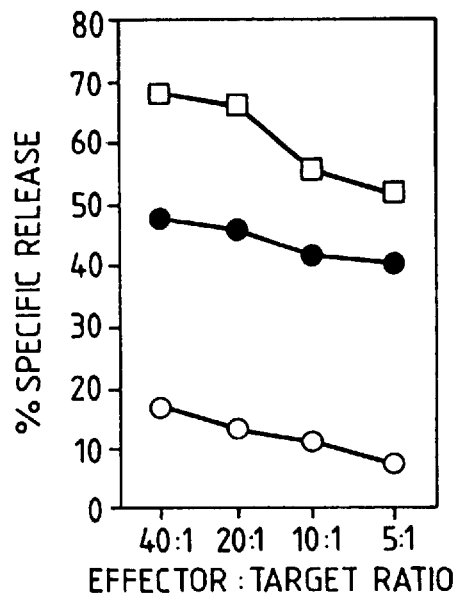
FIG. 5A    FIG. 5B
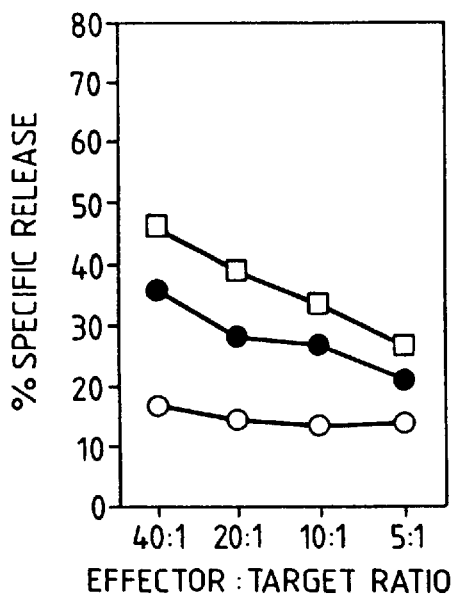 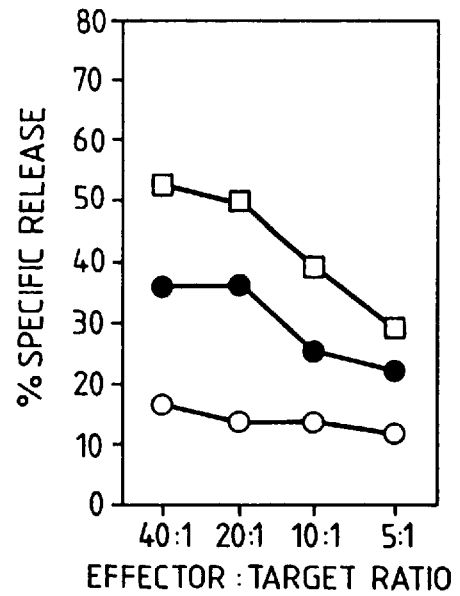
FIG. 5C    FIG. 5D

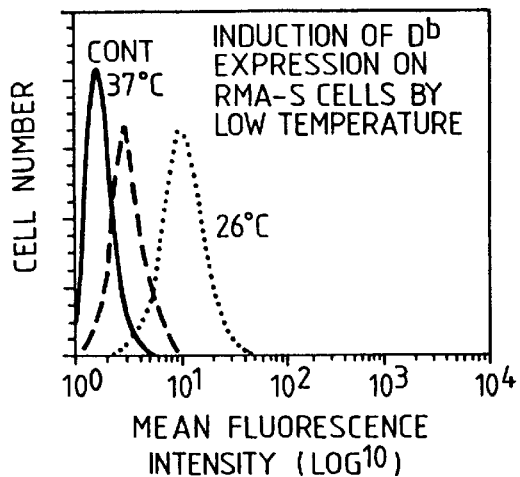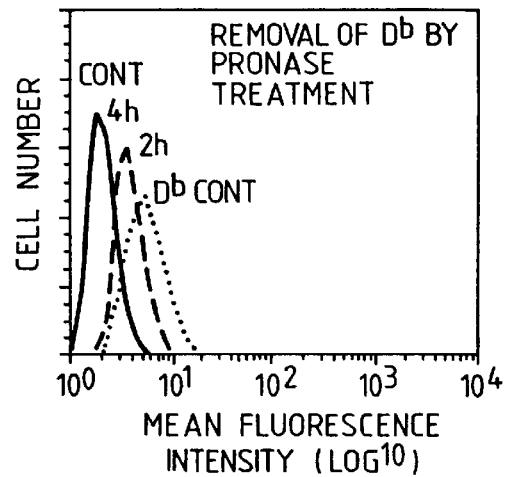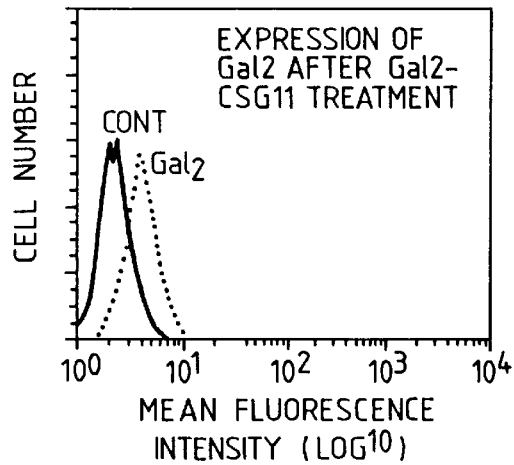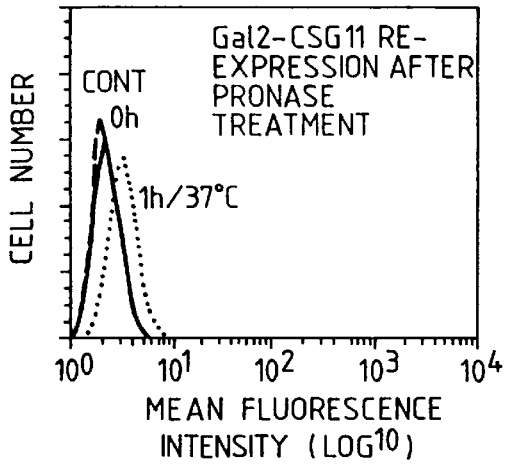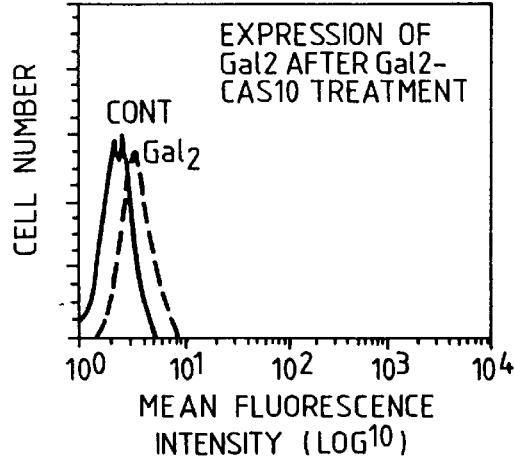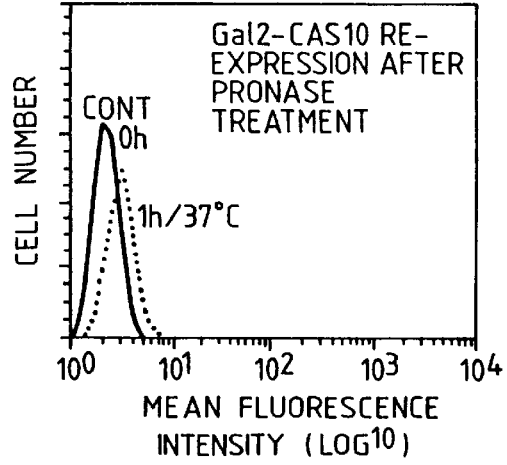

Gal-Gal-SGV-12

FIG. 12

COMPOSITIONS FOR GENERATING T CELL IMMUNITY AGAINST CARBOHYDRATE STRUCTURES

TECHNICAL FIELD

The present invention relates a novel class of biologically active compounds, to processes for their production and to their use in therapy. More particularly the invention provides immunogenic conjugates useful for generating T cell immunity against tumor-associated carbohydrate structures or against carbohydrate structures expressed on infectious agents and/or infected host cells.

BACKGROUND ART

Cell-mediated immunity

The vertebrate immune system is constantly active against invading microbes and malignant cells. It is well known that the adaptive immune system shows a much stronger response on second, as compared to first, encounter with an antigen. This fact is exploited in vaccination, which works by inducing a state of lasting immunity known as immunological memory. Immunological memory requires the activation of T lymphocytes, specific for the infectious agent. T lymphocytes detect infection within cells by recognizing—via the T-cell receptor (TCR)—peptide fragments derived from the pathogen. However, most T lymphocyes are "MHC restricted", i.e. they recognize only complexes of peptides I bound to highly polymorphic membrane proteins, encoded by class I and class II genes of the major histocompatibility complex (MHC) and presented on the surface on an accessory cell (designated an antigen-presenting cell or APC), in which the antigen has been processes. T lymphocytes can be classified as $CD4^+$ or $CD8^+$, depending on the specificity of an adherence receptor molecule. The CD4 adherence receptor recognizes MHC class II molecules, while CD8 binds class I. In addition, MHC restriction is further dependent on direct binding of the MHC molecule to certain parts of the TCR (Jorgensen et al., 1992).

$CD4^+$ T cells (Helper T cells) activate macrophages and antibody-producing B cells, while $CD8^+$ T cells (Cytotoxic T cells, CTL) kill cells infected b viruses and intracellular bacteria. Antigens can be processed by one of wo pathways, depending on their origin. In the first pathway foreign material from outside the cell is engulfed by a specialized antigen-presenting cell (often a macrophage or B-cell), which breaks down the material and links the processed antigen to class II MHC molecules. The complexes are transported to the cell surface and presented to Helper T cells. The second pathway is generally concerned with processing of proteins made within virus-infected or malignant cells. These problems are processed in the cells, i.e. they are subjected to partial proteolysis so as to form peptide fragments. These fragments then associate with class I MHC molecules and are transported to the cell surface for presentation to Cytotoxic T cells.

The processing of antigens by separate pathways makes biological sense. Thus antigens taken up from the surroundings eventually elicit B cells to produce antibodies which will be capable of protecting the organism against a subsequent challenge by the exogenous antigen. On the other hand, in the case of antigens in the form of abnormal structures made within an abnormal or errant cell (for example a virus-infected or malignant cell), it is advantageous for the immune system to be activated with a result leading eventually to the killing of the errant cell.

MHC-binding peptides

In recent years there has been considerable progress in the analysis of peptides bound to MHC class I and II molecules (For reviews see e.g. Janeway, 1991; Rötzschke & Falk, 1991; Stauss, 1991; Tsomides & Eisen, 1991). Thus it has been found that MHC class I molecules bind short peptides of only about 8–12 amino acids and that MHC class II molecule bind peptides of about 10–17 amino acids.

Furthermore it has been found that the peptide fragments resulting from processing of antigens are transported to the cell surface bound in a groove on the extracellular part of an MHC molecule. For MHC class I molecules it has been found that individual amino acid side-chains, located a precise positions along the peptide, bind into the peptide-binding groove (Madden et al., 1991). The position of these pockets and the amino acids that line them can be different for different allelic variants. Consequently, different MHC class I molecule can bind a different set of peptides, and allele-specific motifs have been found for various IHC alleles (Van Bleek & Nathenson, 1990; Falk et al., 1991; Jardetzky et al., 1991). For example, peptides binding HLA-A2.1 preferably have L or M in position 2 and V or L in position 9, i.e. in the C-terminal position (Rötzschke & Falk, 1991).

Examples of peptides capable of binding MHC class I molecules in the murine system are ASNENMETM and SGPSNTPPEI, (SEQ ID NOS: 1 and 2), which both are presented by $H-2-D^b$ molecules. An example of a peptide capable of binding an MCH class I molecule in the human system is GILGFVFTL, (SEQ ID NO: 3), which is presented by HLA-L2.1 molecules (Falk et al., 1991).

Conjugation of a MHC (class II) binding peptide, DYGILQINSR, (SEQ ID NO: 19), to a carbohydrate, 4-O-α-D-galactopyranosyl-β-D-galactopyranose, is described in Elofsson et al. (1991). WO 89/07448 discloses compositions for modulating the immune response of a host, employing peptides having homology with peptides binding MHC class I molecules.

Synthetic peptides as carriers for T cell specific epitopes

CTL:s can be generated from spleens of mice painted with trinitrochlorobenzene (TNP), and selected for killing of TNP-coated syngenic target cells. Some CTL:s generated like this have been shown to recognize short MHC class I ($K^b$)-bound peptides of 10 amino acids with TNP bound to an internal (position 6) lysine residue. Furthermore, some CTL:s kill syngenic target cells that have processed and presented TNP bound to different carrier proteins (MSA, BSA and KLH) and also TNP-coated, allogenic target cells (Ortmann et al., 1992)

Tumor-associated antigens

The possibility that tumors may be recognized as foreign by the immune system (based on the abnormal character of tumor cells) would offer valuable opportunity for developing effective cancer therapies. In experimental systems tumors have shown to be highly immunogenic and the triggered immune responses was sufficient to eliminate the tumor cells. In the clinical situation, however, a tumor, being a product of multiple genetic and adaptive alterations, has little immunogenicity at the time when it becomes a medical problem. Accordingly, few truly tumor associated protein antigens, i.e. antigens being expressed in tumor cells only, have been found.

In contrast to the lack of tumor associated protein antigens, a variety of abberant carbohydrate (CHO) structures are present on tumor cells (for a review see Hakomori, 1991). These are formed as a consequence of abnormalities in the enzyme systems responsible for the assembly of the CHO chains. The chains are often truncated with the result that CHO epitopes (which are absent or hidden on normal cells) are expressed on tumor cells.

Aberrant CHO structures on tumor cells can exist in the form of glycoprotein, glycolipid or a complex of both of these two forms. Glycoproteins are often secreted into body fluids whereas glycolipids to a large extent are membrane bound.

Examples of tumor associated carbohydrate antigens are the GM3 ganglioside, which has been identified in mouse melanoma B16 cells (Nores et al., 1987), GD3 ganglioside associated with human melanoma cells (Portoukalian et al, 1979) and Gb3 ganglioside which is expressed in Burkitt lymphoma cells (Wiels et al., 1981; Brodin et al., 1988).
Carbohydates associated with infectious diseases Carbohydates associated with infectious diseases can be expressed on the infectious agents, on secreted or shed material from these, or on the surface of infected host cells.

There are some examples of verified, or putative, carbohydrate-specific T cell responses, associated with diseases caused by infectious agents like *Salmonella typhimurium* (Robertsson et al., 1982), *Leishmania major* (Moll et al., 1989), *Candida albicans* (Domer et al., 1989) and Mycobacteria (Crowle, 1988).

Carbohydrate antigens associated with HIV infection are described in Hansen et al. (1990).
Immunotherapy against tumors Immunotherapy against tumors has a long medical history and has been tried by both non-specific and specific means. In non-specific manipulations, the immune system has been activated by various factors such as BCG, IL-2 etc., in order to increase the existing background immunity against the tumor. In specific manipulations, vaccines have been constructed using tumor cells or material derived from these.

T cell-mediated immune responses play crucial roles in antitumor immunity. Whereas the mechanisms of activation of T cell responses against proteins are characterized to some extent (see above), they are essentially unknown for carbohydrates. Carbohydrate antigens are poor candidates for presentation to MHC molecules, because of structural constraints imposed by the peptide-binding groove of the MHC proteins. Nevertheless, Ishioka et al. (1992) has shown that the CHO moiety can be an important part of the antigenic determinant recognized by T cells, and suggest that although there are limitations to the generation of CHO-specific T cell responses, such responses could be generated by judicious placement of the carbohydrate within a MHC-binding peptide.

Longenecker and coworkers (WO 88/00053; Henningson et al., 1987) describe the use of "Synthetic Tumor-Associated Glycoconjugates" (S-TAGs) for stimulation of anticancer T cell immunity. In these experiments, synthetic Thomsen-Friedenreich (TF) and Tn antigens, carbohydrates expressed on most human adenocarcinomas, were conjugated to a carrier protein and used to demonstrate that delayed-type hypersensitivity (DTH) effector cells could recognize and respond to the carbohydrate determinants. An S-TAG composed of TF antigen coupled to carrier (keyhole limpet hemocyanin) and emulsified in Ribi adjuvant was administered to mice with TA3-Ha adenocarcinoma. When administration was preceded by treatment with cyclophosphamide, a 50–90% long term survival of the hosts was observed (Fung et al., 1990).

Thurin et al. (1991) describe a conjugate comprising (i) a tumor-associated carbohydrate hapten; (ii) a peptide containing a viral mouse Helper T cell epitope; and (iii) a Quil-A glycoside based adjuvant. Mice immunized with the conjugate showed IgM responses specific for the hapten together with a Helper T cell reactivity to the viral epitope.

SUMMARY OF THE INVENTION

A main object of the invention is to provide a means for generating T-cell immunity against a carbohydrate structure, in particular antitumor immunity against carbohydrate antigens.

Although the prior art suggests that antitumor immunity against carbohydrate antigens may be raised with a synthetic vaccine, in practice the achievement of this aim has remained elusive. For example Longenecker's S-TAGs (described in the section above) utilize a conventional protein as a carrier of the carbohydrate structure. Such a glycoprotein has to be proteolytically cleaved before it can be presented on the cell surface, which means that there is no control over what is finally presented to TCR. In addition, a large carrier protein contains several different epitopes, competing for T cells.

Further, despite major research, prior art efforts to develop immunological therapies for cancer have had disappointing results. Also, prior art procedures for stimulating immune responses against carbohydrate-associated antigens have had limited success, especially in cases where it is desired to stimulate an immune response against a disease-associated carbohydrate structure, for example one expressed on tumor cells, but not on normal cells.

The present invention rises above the prior art by providing a novel class of conjugates comprising MHC class I binding peptides together with a carbohydrate structure which can be used, inter alia, in the development of synthetic vaccines for elliciting anti-tumor immunity. Further the conjugates according to the invention are capable of generating cytotoxic T cell, instead of helper T cell, responses against such carbohydrate structures. Further the conjugates according to the invention permit a higher degree of control (1) over the identity of presented epitope and (2) over which T cell clones will be expanded.

A further object of the present invention is to enable the production of carbohydrate-specific T cells, i.e. cytotoxic T cells generated by the use of class I MHC-binding peptides. The carbohydrate-specific T-cells generated according to the invention need not be MHC-restricted. Accordingly, cells generated in one individual can react with cells from another individual, from the same or even from another species.

The generation of carbohydrate-specific T-cells according to the invention is thus quite different from prior art experiments where a generated Helper T cell response is directed to a peptide epitope, as where haptens are conjugated to carrier proteins in order to achieve antibody response against the hapten or where Thurin et aL extended this concept to the use of defined MHC class II-binding peptides.

As indicated, the purpose of the invention has been achieved by conjugating a suitable peptide capable of binding a MHC class I molecule, to a suitable carbohydrate structure. By conjugating the carbohydrate to the peptide in an optimal position, the carbohydrate antigen can have a high affinity to TCR, which can make the response independent of adherence receptors, i.e. the T cell will not be MHC restricted. This will create CHO-specific responses from both cytotoxic, as well as helper, T cells.

The conjugates according to the invention can be used for treatment of malignant diseases, including melanoma, breast cancer, lung cancer and gastrointestinal cancer. They can further be used for treating diseases by infectious agents causing expression of the carbohydrate target molecule.

The conjugates of the invention can be used for inducing T cell responses in vivo in order to eliminate tumors and/or infections. They can also be used for inducing T cell responses in vitro, using an extra-corporal stimulation procedure for later reinfusion of activated T cells into patients.

Depending on the type of immune response achieved, the conjugates can be administered once or if necessary by continous, regular immunizations.

DETAILED DESCRIPTION OF THE INVENTION

According to a first aspect of the invention there are provided conjugate capable of generating T cell immunity against a carbohydrate structure, said conjugate comprising (i) a peptide component capable of binding a MHC class I molecule; and (ii) a carbohydrate component having the immunogenic specificity of said carbohydrate structure.

The invention further provides a method of stimulating the production of cytotoxic T cells (CTLs) in a patient, wherein said CTLs have the potential to destroy or attenuate cells presenting a characteristic disease-associated carbohydrate structure, which comprises administering to the patient an effective dose of a conjugate as herein defined.

Also provided according to the invention is a method of producing cytotoxic T cells (CTLs) which have the potential to destroy or attenuate diseased associated cells presenting a characteristic disease-associated carbohydrate structure, which comprises contacting a cell population with a conjugate as herein defined, wherein said cell population includes (a) cells possessing MHC class I molecules capable of binding to the peptide component of said conjugate and (b) cells capable of being converted to CTLs having the said potential on interaction with cells (a) having said conjugate bound to a MHC class I molecule.

CTLs may be produced in the manner described by administering the peptide/carbohydrate conjugate to an animal whereby the CTLs are produced in vivo. Alternatively the CTLs may be produced in vitro by contacting cells which have been removed from the animal body with the peptide/carbohydrate conjugate. The so-produced CTLs may then be administered (e.g. by introducing them into the same or a different animal) part of a therapeutic regime.

The invention further provides the use of the peptide/carbohydrate conjugate described herein for the manufacture of pharmaceutical compositions.

More specifically there is provided the use of the conjugates for the manufacture of a pharmaceutical composition for inducing a desired immunological state in a patient, wherein said immunological state results from an interaction between said conjugate and an MHC class I molecule whereby a cellular component of the immune system is stimulated to induce a response specifically associated with said carbohydrate structure.

Preferably the peptide component and the carbohydrate component and the carbohydrates according to the invention have the characteristics set forth in the following paragraphs.

The Peptide component

An important feature of the peptide/carbohydrate conjugates of the invention is that the peptide component thereof should be capable of binding a MHC class I molecule. For a given peptide, the capability to bind a MHC class I molecule may be determined in a number of ways. Thus for example the peptide may have certain selected structural characteristics such as size or the presence of particular amino acids residues in specified positions. Alternatively or additionally the capability of a candidate polypeptide to bind a MHC class I molecule may be assessed empirically by carrying out one or more immunological assays. As a further alternative, the peptide component of the peptide/carbohydrate conjugates of the invention may have a sequence or motif which is substantially identical to the sequence of a peptide which has been isolated by dissociating a naturally-occurring complex between a peptide and a MHC class I molecule. Each of these indicators of the capability of a peptide to bind an MHC class I molecule will be described in further detail below.

Particular reference is made to three articles (Fremont et al, 1992 Matsamura et al 1992 and Latron et at appearing in Science, Vol. 257, 14th Aug. 1992.

These articles describe the characteristics of peptide motifs which are capable of binding MHC class I molecules with particular reference to the murine MHC class I molecule $H-2K^b$ and the human class I molecule HLA-A2 (the latter being present in approximately 40% of the human population).

A characteristic of MHC class I molecules which is associated with their capacity to bind a range of characteristically recognised peptides is the presence of a peptide binding groove which defines a series of generally six so-called "pockets" which accommodate or anchor structural elements of the peptides which are capable of being bound. The peptide binding groove or cleft is limited laterally by two a-helixes while the floor is defined by a β-pleated sheet.

Of the six pockets (normally designated A, B, C, D, E and F) generally two are arranged to accommodate the $—NH_2$ and —COOH termini of the peptide respectively.

The peptide component of the conjugate is preferably chosen from peptides having the optimal number of amino acids for binding MHC class I molecules, ie. 5–25 amino acids, especially 8–12 amino acids, the size being selected to allow for proper binding in the peptide binding groove. The optimal size of the peptide to enable efficient binding in the groove of the MHC class I molecule is 8 or 9 amino acids, with 9 amino acids being especially preferred.

Most preferably the peptide component of the conjugates of the invention have a hydrophobic amino acid in the C-terminal position to facilitate binding in pocket F. Other amino acids of the peptide component are preferably selected so as to fit within other pockets in the peptide binding cleft. Selection of suitable and preferred amino acid residues may be aided by computer-based molecular modelling techniques as described e.g. by Masazumi (1992).

The peptide can be synthesized by known methods. The immunogenicity of the peptide part of the conjugate can be further increased by chemical modifications. Conjugates comprising such modified peptides are part of the invention.

Peptides to be synthesized can be chosen from those known from the literature or from those which immunogenicity are determined by known methods. In the latter case peptides can be isolated from whole-cell lysates or from purified MHC molecules and separated by e.g. high-performance liquid chromatography. Optimal binding of the peptide to the MHC molecule is reflected as high stability of the peptide-MHC complex on the surface of antigen-presenting cells.

The invention further provides a process for producing a peptide/carbohydrate conjugate as defined above which comprises one or more of the following procedure steps:
  (a) synthesizing the peptide component of the conjugate by a known technique of peptide synthesis,
  (b) synthesizing the carbohydrate component of the conjugate by a known technique of carbohydrate synthesis, (c) protecting one or more —COOH, OH, —NH$_2$ or —SH groups of the peptide component prior to coupling the peptide component covalently to the carbohydrate component, (d) protecting one or more —OH, —COOH, —NH$_2$, —CHO or =CO groups of the carbohydrate component prior to coupling the carbohydrate component covalently to the peptide component, (e) activating an unprotected —OH, —COOH, —NH$_2$, —CHO, or =CO group of the carbohydrate component, (f) activating an unprotected —OH, —COOH, —NH$_2$, or —SH group of the peptide component, (g) reacting at least one of the carbohydrate component and the peptide component with a bifunctional linking reagent, (h) reacting the carbohydrate component and the peptide component covalently so as to form the desired conjugate, said components being suitably protected, activated and/or reacted with a bifunctional linking reagent, (i) subjecting an intermediate protected peptide/carbohydrate conjugate to a deprotecting procedure.

In the present context, a peptide "capable of binding a MHC class I molecule", may consequently be further defined as a peptide whose complex with a MHC class I molecule will be stable on the surface of antigen-presenting cells.

Stability of the above mentioned complex can be measured by in vitro assays known to a person skilled in the art. It can be measured as long-term expression on the cell surface, due to a slow decomposition of the complex. Another characteristic reflecting high stability is the sensitization of target cells for corresponding CTL:s at very low concentration of the peptide. Stability can also be reflected as the capacity of peptides to upregulate the expression of the corresponding class I molecule on certain target cells in vitro at low molar concentrations.

Stability is also related to high immunogenicity in vivo, when short peptides are directly injected into mice.

The capacity of a glycopeptide to be bound by an MHC class I molecule may be assessed by carrying out immunological assays designed to detect one or more of the following characteristics (1) glycopeptide binding to soluble MHC-I leading to the formation of complexes which may, for example, be detected by configuration-dependent monoclonal antibodies, or by association with labelled β$_2$microglobulin, using conventional biochemical techniques;

(2) expression of the CHO part after the glycopeptides have bound to empty MHC-I molecules on the surface of mutant host cells (such as RMA-S and T2 cells). The CHO part may then be detected by CHO-specific monoclonal antibodies such as MC2102 (Gal$_2$ specific).

(3) upregulation of the corresponding MHC-I restriction element by glycopeptides, using MHC-I specific monoclonal antibodies.

(4) the recycling capacity of the glycopeptides (see Section 3 below —"E)CTERNAL MHC-1 BINDING PEPTIDES ARE RECYCLED TO THE CELL SURFACE AFTER INTERNALIZATION")

In order to carry out these assays use may be made of available antibodies which are capable of detecting MHC class I molecules as well as antibodies which are capable of detecting specific carbohydrates. A particular example of the latter is the commercially available monoclonal antibody MC2102 (New Biocarb, Lund. Sweden) which is capable of detecting the carbohydrate Gal$_2$.

These procedures may be used to assess the capacity of a given peptide to be bound by MHC class I molecules in the following manner.

First a glycopeptide is synthesised in which Gal$_2$ is covalently linked to the peptide. The glycopeptide may then be tested for its capacity to bind to MHC class I molecules on target antigen-presenting cells, and for the carbohydrate part to be expressed, i.e. bound in a configuration in which the Gal$_2$ epitope is located in a position in which it can be detected by a specific antibody. Additionally upregulation of the corresponding MHC-I restriction element may be assessed by determining the capacity of the antigen-presenting cells to interact with anti-MHC class I antibodies.

The capacity of the conjugate to be recycled may be assessed by incubating the cells (with bound conjugate) at 37° C. whereupon the glycopeptide will internalise. The temperature may then be lowered and the cells treated with a proteolytic enzyme (e.g. Pronase) to strip off exposed peptide/carbohydrate conjugate. On reheating, recycled conjugate may be detected by probing for the $Gal_2$ epitope using the anti-$Gal_2$ antibody.

In a further test, the conjugate can be tested in immunisation experiments and assessed for its capacity to stimulate the formation of CTLs. In control experiments the generated CTLs can be tested against the peptide component (without the carbohydrate component) to demonstrate that the observed CTL-stimulation is associated with the carbohydrate (see "Experimental Test System"below).

The carbohydrate component

The carbohydrate part of the conjugate may be synthesized by known methods and is preferably chosen from carbohydrate structures that:

(a) are stably expressed on the target cell so that the same part always is exposed outwards to the T cell receptor;

(b) have a high density on the target cell so that the T cell receptor can be triggered independently of MHC restriction and adherence receptors; and (c) have a high membrane association so that secretion into the general circulation is avoided. Soluble carbohydrates are, in contrast, likely to create problems because of induction of peripheral suppressor T cells and blocking of the generation of protective immunity.

A further advantage with chosing a carbohydrate with high expression on target cells is that such high expression may lead to secondary modifications in the membrane which increase the target cell specificity of the exposed CHO epitopes.

The carbohydrate should be sized to enable the T cell receptor to encompass a CHO epitope. A preferable size, to which the invention however is not restricted, is half the length of the peptide.

Although single sugar moieties are not excluded, preferably the carbohydrate component of the conjugates of the invention will contain at least two linked sugar moieties, i.e. it will be a di-saccharide or oligo saccharide. The precise number of linked sugar moieties will be dependent on the immunogenic specificity of the carbohydrate structure, but 3, 4, 5 or more linked sugar moieties may be present.

Preferably the upper limit on the size of the carbohydrate component will be dictated by the requirement that it should be sized to enable a T cell receptor to simultaneously encompass an epitope of the carbohydrate structure and also the Class 1 restriction element. Typical upper limits are not more than 10 sugar moieties, preferably not more than 8 and most preferably not more than 5. Preferred ranges are thus from 1 to 10, more preferably from 1 to 8 and most preferably from 1 to 5 sugar moieties. For each of these preferred ranges, the lower limit of 1 may be increased to 2, 3, 4 or 5 if desired.

The individual sugar moieties are preferably selected from aldopentoses, ketopentoses, aldohexoses and ketohexoses. These may be in linear or cyclised form and if desired, derivatised by oxidation, reduction, amination, acetylation or any combination of these. Oxidation can include conversion of one or more —$CH_2OH$ groups to —CHO or COOH groups, as well as conversion of a —CHOH— group to a —$CH_2$— group. Reduction can include any of the reverse conversions. The aldopentoses include D-ribose, D-arabinose, D-xylose and D-lyxose as well as other stereo-isomers thereof, i.e. the L-isomers. The aldohexoses include D-allose, D-altrose, D-glucose, D-mannose, D-gulose, D-idose, D-galactose and D-talose as well as other stereo-isomers thereof, i.e. the L-isomers. The ketopentoses include D-ribulose and D-xylulose as well as; other stereo-isomers thereof, i.e. the L-isomers. The ketohexoses include D-psicose, D-fructose, D-sorbose and D-tagatose as well as other stereo-isomers thereof, i.e. the L-isomers. When cyclised, the sugar moieties can be in the α- or β- configuration and (if appropriate) in the pyranose or furanose forms.

Most preferably the carbohydrate component contains one or more sugar moieties selected from ones normally found in the carbohydrate portions of glycolipids and glycoproteins. These include β-L-fucose (Fuc), β-D-galactose (Gal), β-D-N-acetylgalactosamine (Gal NAC), β-D-N-acetylglucosamine (Glc NAC), β-D-mannose (Man), neuramic acid (Neu) and sialic acid (Sia).

Carbohydrate components corresponding to the CHO portions of the globo/ganglio series of glycolipids are further examples of suitable tumor targets, as they are mostly membrane-associated and are not secreted. (see Oettgen, 1989; Chapter 6 "General Concept of Tumor-associated Antigens: Their Chemical, Physical, and Enzymatic Basic").

The mode of linking adjacent sugar moieties is not critical, i.e. linkages can be eflected utilising any of carbon atoms 1 to 5 of pentoses and any of carbon atoms 1 to 6 of hexoses. Further the linkages can be either a or β. Most preferably the linkages involve carbon atoms 3 and 4 with the β configuration being preferred.

The carbohydrate component and the peptide component can be conjugated (or linked covalently together) by any convenient means. Where the peptide component includes an amino acid bearing a hydroxyl group (i.e. as in serine, threorine or tyrosine) the linkage can be via an O-glycoside bond. Where the peptide component includes an amino acid containing an —$NH_2$ side chain (as in asparagine) the linkage can be via an N-glycoside linkage.

Alternatively the linkage can involve the introduction of a so-called "spacer arm" between the carbohydrate component and the peptide component. Thus, for example where the peptide component includes an amino acid (cysteine) having an —SH side chain, the carbohydrate component can be linked to the —SH side chain via a —$(C_nH_{2n})$—O— linkage wherein n is >2, preferably 2 to 4.

The location of the carbohydrate component on the peptide/carbohydrate conjugate is preferably chosen so that when bound to an MHC class I molecule, the carbohydrate component occupies a generally central location in the peptide binding groove, with at least part of the carbohydrate component protruding from the groove in a manner enabling it to be presented to a CTL.

Examples of Carbohydrates suitable for conjugation

Examples of carbohydrate structures, associated with human tumors or infectious diseases, and suitable for conjugation are given below in Table 1. The indicated tumors exemplify types of cancer susceptible to treatment with the conjugates of the present invention. For the purpose of this description, the term "carbohydrate structures" is to be understood as comprising derivatives of the exemplified carbohydrates, such as e.g. lactones and lactams.

TABLE 1

1. CARBOHYDRATES ASSOCIATED WITH HUMAN TUMORS:

1.1 The majority of tumors:

| | |
|---|---|
| Galβ4GlcβCer | Lactosylceramid |

1.2 Melanoma:

| | |
|---|---|
| NueAcα8NeuAcα3Galβ4GlcβCer | GD3 |
| 9-O-Ac-GD3 | |
| NeuAcα8NeuAcα3(GalNAcβ4)Galβ4GlcβCer | GD2 |
| 9-O-Ac-GD2 | |
| Lactonized forms of these | |

1.3 Colon cancer and other types of cancer:

| | |
|---|---|
| GalNAcα-Ser(Thr) (glycoprotein) | Tn-antigen |
| NeuAcα6GalNAcα-Ser(Thr) | Sialyl-Tn-antigen |
| Galβ3GlcNAc | Type 1 chain |
| NeuAcα3Galβ3(Fucα4)GlcNAcβ | Sialyl-Lewis a |
| NeuAcα3Galβ3(Fucα4)[NeuAcα6]GlcNAcβ | Disialyl-Lewis a |
| Galβ3(Fucα4)GlcNAcβGalβ3(Fucα4)GlcNAβ | Dimer Lewis a |
| NeuAcα3Galβ4(Fucα3)GlcNaβ | Sialyl-Lewis x |
| Galβ4(Fucα3)GlcNAcβ3Galβ4(Fucα3)GlcNAcβ | Dimer Lewis x |
| Galβ4(Fucα3)GlcNAβ3Galβ4(Fucα3)GlcNAcβ | Trimer Lewis x |
| 3Galβ4(Fucα3)GlcNacβ | |
| NeuAcα3-Dimer Lewis x | |
| NeuAcα3-Trimer Lewis x | |
| NeuAcα6-Oligomer Lewis x | |
| Lactonized forms of these in the case of sialic acid | |

1.4 Lung cancer and other types of cancer:

| | |
|---|---|
| Galβ4GlcNAcβ3Galβ4GlcNAcβ | i-antigen (rep. lactosamine) |
| Galβ3(Fucα4)GlcNAcβGalβ4(Fucα3)GlcNAcβ | Lewis a - Lewis x |
| Fucα2Galβ3GalNAcβ4(NeuAcα3)Galβ4GlcβCer | Fuc-GM1 |
| Lactonized forms of Fuc-GM1 | |

1.5 Burkitt's Lymphoma:

| | |
|---|---|
| Galα4Galβ4GlcβCer | Gb3 |

1.6 Breast Cancer:

| | |
|---|---|
| Fucα2Galβ3GalNAcβ3Galα4Galβ4GlcβCer | Fuc-Globopenta |
| Tn-antigen | |
| Sialyl-Tn-antigen | |

1.7 Teratocarcinoma:

| | |
|---|---|
| NeuAcα3Galβ3GalNAcβ3Galα4Galβ4GlcβCer | Sialyl-Globopenta |
| Lactonized form of the above | |

2. CARBOHYDRATES ASSOCIATED WITH EXPERIMENTAL TUMORS:

2.1 Melanoma (Hamster):

| | |
|---|---|
| NeuAcα3Galβ4GlcβCer | GM3 |
| GD3 | |
| 9-O-Ac-GD3 | |
| GD2 | |
| Lactonized forms of these | |

2.2 Melanoma (Mouse):

GM3
Lactonized GM3

3. CARBOHYDRATES ASSOCIATED WITH INFECTIOUS AGENTS

Mannan from *Candida albicans*
Polysaccharide isolates from *Mycobacterium bovis* strain BCG
Lipophosphoglycan from *Leishmania major*
O-antigenic polysaccharides from *Salmonella typhimurium*

TABLE 1-continued

4. CARBOHYDRATES ASSOCIATED WITH HIV

| | |
|---|---|
| Fucα2galβ4(Fucα3)GlcNAcβ | Lewis y |
| GalNAcα3(Fucα2)Galβ3GlcNAcβ | Blood group $A_1$ |
| NeuAcα6GalNAcα-Ser(Thr) | Sialyl $T_n$ antigen |
| GalNAcα-Ser(Thr) | $T_n$ antigen |

Preferred characteristics of the conjugate

The carbohydrate can be coupled to the carrier peptide aminoterminally, carboxyterminally, or it may be coupled to internal amino acids. As indicated, internal coupling is preferred.

Also, as described above, specific anchoring amino acids, binding in pockets on the MHC molecule, have been defined in the literature for peptides binding various MHC molecules. These anchoring amino acids should preferably not be used for conjugation to the carbohydrate structure.

The synthetic carbohydrate should have a high degree of molecular stability when conjugated to the carrier peptide, in order to expose the carbohydrate epitopes with high specificity. The position of the carbohydrate in the conjugate should be such that the T cell receptor can recognize a CHO epitope, in order to generate optimal triggering of T cells.

Further, the size and position of CHO should be optimal for recognition by TCR, especially by the third complementarity determining region (CDR3). A preferable position, to which the invention however is not restricted, is centrally in the glycopeptide.

The CHO and peptide may be conjugated via optional linker elements. Such linker elements can be additional amino acids, e.g. cysteine, or other suitable chemical compounds.

Experimental test system

The immuriogenicity of the conjugates of the invention can be tested in immunization experiments known to a person skilled in the art. CHO specificity can be analyzed by "criss-cross" experiments: T-cells that respond to the conjugate "CHO-A", wherein A designates a peptide, are tested with CHO-A; peptide A alone; CHO-B, wherein B designates a peptide different from A; and peptide B alone. If e.g. CTL responding to CHO-A also kill cells presenting CHO-B, but not cells presenting peptides alone, the response can be concluded to be CHO-specific. In addition, T cells may be tested against target cells expressing the CHO part in the form of a glycolipid.

Pharmaceutical formulations

The conjugates according to the invention can be administered in conventional dosage forms. When administered in the form of vaccines, it is preferred that they include one or more suitable adjuvants.

It has been found that administration of peptide/carbohydrate conjugates according to the invention can result in binding of the conjugates to empty MHC molecules on the cell surface. Such a binding is possible since the glycopeptide has in effect been synthetically pre-processed, i.e. it does not have to enter the cytosol to be processed.

Alternatively, the conjugates can be incorporated into a structure able to facilitate transport into the cytosol, in order to achieve early binding to the MHC molecule. Such structures can be liposomes or "immunostimulating complexes" (iscoms) (Morein et al., 1984).

The following examples illustrate the synthesis of conjugates according to the invention.

EXAMPLES

1. PREPARATION OF GLYCOCONJUGATES

1.1. Synthesis of glycopeptides

Glycopeptides can be synthesized by e.g. coupling preformed spacer arm glycosides with peptides containing a thiol function.

Thus, a cysteine moiety was introduced in the peptide sequence and the nucleophilic properties of the cysteine sulphur atom was utilized to create a thioether linkage between the peptide and an electrophilic spacer arm glycosidically linked to the carbohydrate moiety. The spacer arms used were the 3-bromo-2-bromomethylprop-1-yl (DIB) (Magnus 1982) and 2-bromoethyl (Dahmén et al., 1983 b) groups. By this strategy it was possible to couple carbohydrates representing various epitopes and antigenic determinants to the same peptide sequence. The latter could in turn be obtained by standard peptide synthesis techniques and assayed for biological activity prior to conjugation. Thus, time required for peptide syntheses was kept at a minimum.

The coupling reactions were performed in dimethylsulfoxide or N,N-dimethylformamide.

Prior to coupling, hydrogen bromide was eliminated from the DIB group using N,N,N,N-tetrabutylammonium fluoride (Magnusson et al., 1982). The allylic bromide obtained was then reacted with the cysteine containing peptide. Due to side reactions, such as formation of unreactive allylic fluorides, this method did not allow the excess of the carbohydrate derivative used to be recovered.

Cesium carbonate was used as a promoter when 2-bromoethyl glycosides were employed (Dahmen et al., 1983 b).

The amount of N,N,N,N-tetrabutylammonium fluoride or Cesium carbonate needed for coupling was dependent on included trifluoroacetic acid in the peptides used. The amount of trifluoroacetic acid included varied depending on the batch and structure of the peptide. The choice and amount of solvent was determined by the solubility properties of the peptide.

The coupling reactions were monitored by HPLC and were quenched by the addition of water containing 0.1% trifluoroacetic acid. The resulting glycopepticles were purified by preparative HPLC and the molecular weights of the products were confirmed by FAB MS.

Both saturated and allylic bromides have been reported to react with cysteine thiols in unprotected peptides to give, as major products, S-alkylated peptides.

Yang et al. (1991) prepared farnesylated peptides by reacting cysteine containing octa- and pentadecapeptides with farnesyl bromide at pH 6–9 in mixtures of N,N-dimethylformamid/dimethylsulfoxidlacetonitril. N,N-diisopropylethylamine was used as a promoter. Exclusive S-alkylation was reported even at pH 10–12.

Selective S-alkylations of cysteine-containing peptides was also performed (Or et al., 1991) in methanolic or ethanolic ammonia using various alkylating agents, e.g. a primary bromopropyl derivative.

1.2. Synthesis of the spacer arm glycosides (FIGS. 1 and 2)

The spacer arm glycosides used for coupling are exemplified by the DIB β-glycoside and the 2-bromoethyl β-glycoside of NeuNAcα3Galβ4Glc (3"-sialyllactose), the 2-bromoethyl β-glycosides of Galα4Gal and Galα4Galβ, 4Glc and the 2-bromoethyl glycoside of "GM3 Lactam" (Compounds 9, 15, 28 48 and 55 respectively).

DlB β-glycoside of 3"-sialyllactose (9) was synthesized in eleven steps from 2-trimethylsilylethyl 2,3,6-tri-O-acetyl-4-O-(2,3,4,6-tetra-O-acetyl-β-D-galactopyranosyl)-β-D-glucopyranoside (1) (Jansson et al., 1988). Deacetylation of (1) gave (2) which was isopropylidenated and benzylated to give the benzyl protected 3',4'-O-isopropylidene lactose derivative (3). Hydrolysis of the 3',4'-acetal gave the glycosyl acceptor (4) in an overall yield of 51%. Glycosylation (Marra and Sinaÿ, 1990) of the lactose derivative (4) in acetonitrile at −23° C. using the acetyl protected α-xanthate (5) (Marra and Sinay, 1989) of sialic acid methyl ester as a glycosyl donor and dimethyl(methylthio)sulfonium trifluoromethanesulfonate (DMTST) as a promoter gave, after debenzylation and acetylation, the trisaccharide derivative (6) in a yield of 17.5%. The ease of purification and the yield of (6) were slightly improved when acetylation of unreacted hydroxy functions of the reaction products was performed before hydrogenolysis of the benzyl ethers. The 2-trimethylsilylethyl glycoside (6) was converted (Jansson et al., 1988) to the corresponding 1 β-acetate (7) which was used as a glycosyl donor in a Lewis acid catalyzed glycosylation of 3-bromo-2-bromomethylpropan-1-ol yielding the protected β-glycoside (8) in 46% yield. Deprotection of (8) by methanolic sodium methoxide followed by aqueous methanolic sodium hydroxide gave the DIB β-glycoside of 3″-sialyllactose (9) which, after elimination of HBr to give the corresponding 2-bromomethylprop-2-en-1-yl glycoside, was used for coupling to peptides.

The 2-bromoethyl β-glycoside of 3″-sialyllactose (15) was in turn synthesized from the acetyl protected 2-bromoethyl glycoside of lactose (10) (Magnusson et al., 1982) by a five step sequence. Deacetylation of (10) gave (11) which was isopropylidenated (Catelani, 1988) to give the 3,′4′-O-isopropylidene derivative (12) in 86% yield. Partial benzoylation (Murase et al, 1989) at −60° C. followed by hydrolysis of the 3,′4′-acetal gave the 2,6,6′-tri-O-benzoate (13) in 31% yield. The lactose derivative (13) was glycosylated −60° C. (Lonn and Stenvall, 1992) using the xanthate (5) as a glycosyl donor and methylsulfonium trifluoromethanesulfonate (MST) as a promoter to give the protected trisaccharide derivative (14) in a yield of 75%. Deprotection as for 8 gave the 2-bromoethyl glycoside (15) in 96% yield.

1.3. Experimental $^1$H- and $^{13}$C-NMR spectra were recorded in CDCl$_3$ at 300 and 75 MHz respectively on a Varian Gemini 300 spectrometer unless otherwise stated. Signals from undeuterated solvent at 7.25 and 77.0 ppm respectively were used as internal reference signals.

Optical rotations were measured using a Perkin Elmer 241 polarimeter.

Thin layer chromatography was performed on Merck DC-Fertigplatten (Silica gel 60 F$_{254}$ 0.25 mm) and spots visualized by spraying with 10% sulphuric acid followed by charring at elevated temperature and/or spraying with molybdatophosphoric acid/CeSO$_4$/dil. H$_2$SO$_4$ followed by heating (Renaud and Seebach, 1986). Matrex™ Silica Si 0.35–0.70μ was used for preparative chromatography.

HPLC was performed using a Beckman System Gold chromatographic system on a Beckman Ultrasphere C-18 (4.6×150 mm) column with mixtures of acetonitrile-water containing 0.1% trifluoroacetic acid. For preparative runs a Beckman Ultraprep C-18 (10μ, 21.2×150 mm) column was used. Chromatograms were monitored at 214 nm.

2-Trimethylsilylethyl 4-O-β-D-galactopyranosvl-β-D-glucopyranoside (2)

2-Trimethylsilylethyl 2,3,6-tri-O-acetyl-4-O-(2,3,4,6-tetra-O-acetyl-β-D-galactopyranosyl)-B-D-glucopyranoside (1) (Jansson et al., 1988) (29.4 g, 40 mmol) was stirred in methanolic sodium methoxide (5.8 mM, 515 mL) for 15 h. Neutralization with acetic acid, evaporation and crystallization from ethanol gave (2) (14.6 g, 82%).

m.p. 175°–177° C.

$[\alpha]D^{22}$: +18.5° (c 1.0, water)

$^1$H-NMR (D$_2$O, (CH$_3$)$_3$Si(CD$_2$)$_2$COONa) δ: 4.51 (d,1H, J=8 Hz, H-1/H-1′), 4.46 (d, 1H, J=7.5 Hz, H-1H-1′), 4.10–3.50 (13H), 3.30 (t, 1H, J=8.5 Hz), 1.09 (td, 1H, J=13, 13 and 6 Hz, CH$_2$Si), 0.98 (td, 1H, J=13, 13 and 5.5 Hz, CH$_2$Si), 0.04 (s, (CH$_3$)$_3$Si ) ppm $^{13}$C-NMR (D$_2$O, (CH$_3$)$_3$Si(CD$_2$)$_2$COONa) δ: 105.7 (C-1/C-1′), 104.2 (C-1/C-1′), 81.2, 78.2, 77.6, 77.4, 75.7, 75.4, 73.8, 71.4, 71.2, 63.8, 62.9, 20.4 (CH$_2$Si), 0.4 ((CH$_3$)$_3$Si) ppm.

2-Trimethylsilylethyl 2,3,6-tri-O-benzyl-4-O-(2,6-di-O-benzyl-3,4-O-isopropylidene-β-D-galactopyranosyl)-β-D-galactopyranosyl)-β-D-glucopyranoside (3)

To compound 2 (14.5 g, 32.9 mmol) in 2,2-dimethoxypropane (250 mL) was added p-toluenesulphonic acid monohydrate (1.6 g). The mixture was stirred for 165 min. Triethyl amine (9 mL) was then added and the mixture was evaporated. The residue (containing a mixture of acetals) was treated with aqueous 5% acetic acid (100 mL) for 50 min and was then evaporated to give, according to TLC, one major product and traces of a second component (presumably the 4′,6′-acetal).

A part (11.9 g, 25.3 mmol) of the crude product 15.5 g) was dissolved in dry N,N-dimethylformamide under nitrogen. Sodium hydride (60%, 6.16 g, 154 mmol) was added and the mixture was stirred for 1 h. Benzyl bromide (21 mL, 177 mmol) was then added during 15 min. and the stirring was continued for 14 h. The mixture was worked up by addition of methanol followed by water and was then partitioned between dichloromethane and water. The aqueous phase was extracted once with dichloromethane and the combined organic phases were dried (Na$_2$SO$_4$), filtered and evaporated. Chromatography (toluene-ethyl acetate) gave compound 3 (15 g, 73%) as a syrup. $[a]D^{22}$: +16.5° (c 1.2, chloroform)

$^1$H-NMR δ: 7.45–7.25 (25H, Ar-H), 5.0–4.3 (12H, anomeric and benzylic signals), 4.15–3.90 (4H), 3.85–3.30 (10H), 1.42 (s, 3H, CH$_3$), 1.37 (s, 3CH3), 1.14–0.97 (m, 2H, CH$_2$Si), 0.05 (s, (CH$_3$)$_3$Si) ppm.

$^{13}$C-NMR δ: 139.3, 139.0, 138.8, 138,7, 138.6, 128.5–127.4, 109.9 ((CH$_3$O)$_2$C), 103.3 (C-1/C-1′), 102.0 (C-1/C-1′), 83.1, 82.0, 80.7, 79.9, 75.4, 75.1, 74.9, 73.6, 73.4, 73.2, 72.0, 68.9, 68.34, 67.3, 27.8, 26.2, 18.3 (CH$_2$Si), −1.7 ((CH$_3$)$_3$Si) ppm.

2-Trimethylsilylethyl 2,3,6-tri-O-benzyl-4-O-(2,6-di-O-benzyl-β-D-galactopyranosyl)-β-D-glucopyranoside (4)

Compound 3 (14.9 g, 15.9 mmol) in 80% aqueous acetic acid (110 mL) was stirred at 80° C. for 35 min. and was then evaporated. Chromatography (toluene-ethyl acetate, 4:1) gave compound 4 (12.3 g, 86%). An analytical sample was crystallized from heptane.

m.p. 98.8°–100.1° C.

$[\alpha]D^{22}$: +15.6° (c 1.4, chloroform)

$^1$H-NMR δ: 7.45–20 (25H, Ar-H), 5.05–4.56 (7H), 4.50–4.35 (5H), 4.10–3.30 (14H), 2.53 (bs, 1H, OH), 2.45 (bs, 1H, OH), 1.13–0.97 (m, 2H, CH$_2$Si), 0.04 (s, (CH$_3$)$_3$Si) ppm.

$^{13}$C-NMR δ: 139.4, 139.0, 138.6, 138.5, 138.2, 128.7–127.4, 103.3 (C-1/C-1′), 102.7 (C-1/C-1′), 82.9, 82.6, 80.1, 76.7, 75.2, 74.1, 74.9, 73.5, 73.46, 73.2, 72.8, 68.8, 68.6, 68.4, 67.4, 18.3 (CH$_2$Si), −1.7 ((CH$_3$)$_3$Si) ppm 2-Trimethylsilylethyl 2,3,6-tri-O-acetyl-4-O-{2,4,6-tri-O-acetyl-3-O-[methyl(5-acetamido-4,7,8,9-tetra-O-acetyl-3,5-dideoxy-D-galacto-α-D-galacto-2-nonulopyranosyl)onate]-β-D-galactopyranosyl}-β-D-glucopyranoside (6)

Compound 4 (8.8 g, 9.9 mmol), 5 (2.93 g, 4.9 mmol) and powdered molecular sieves (3A, 12 g) in dry acetonitrile (114 mL) was cooled under nitrogen to −23° C. To this mixture was added, with stirring, a solution (50 mL) of dimethyl(methylthio)sulfonate trifluoromethanesulfonate (Marra and Sinay, 1990) (25.7 mmol) acetonitrile (50 mL).

The reaction mixture was stirred at −23° C. for 2 h and was then filtered through celite and partitioned between saturated aqueous sodium hydrogencarbonate and dichloromethane. The aqueous phase was extracted once with dichloromethane and the combined organic phases were dried (Na$_2$SO$_4$), filtered and evaporated. Chromatography (toluene-ethyl acetate-methanol, 35:35:1) gave a fraction (1.96 g) containing one major and two minor components. Acetylation in acetic anhydride-pyridine (1:1) for 12 h gave, after evaporation, a crude product which was subjected to hydrogenolysis at 35 psi for 4.5 h in glacial acetic acid using 10% palladium on charcoal as a catalyst ( 50 mL acetic acid, 0.75 g 10% Pd/C per g of substrate). Filtration, evaporation and chromatography (toluene-ethanol 6:1) gave a major fraction which was acetylated as above. Chromatography (toluene-ethanol, 18:1→10:1) gave amorphous compound 6 (1.0 g, 17.5%).

[α]D$^{22}$: −8.8° (c 1.2, chloroform)

$^1$H-NMR δ: 5.54 (ddd, 1H, J=9.5, 5.0 and 2.5 Hz, H-8"), 5.38 (dd, 1H, J=9.5 and 2.8 Hz, H-7"), 5.17 (t, 1H, J=9.5 Hz, H-3), 5.08 (d, 1H, J=10.5 Hz, NH), 4.97–4.82 (4H, H-2,H-2', H-4', H-4"), 4.62 (d, 1H, J=8 Hz, H-1'), 4.54–4.37 (4H, inter alia H-1, H-3'), 4.18 (dd,1H, J=12 and 5.5 Hz), 4.1–3.8 (10H), 3.83 (s, CH$_3$O), 3.65–3.49 (3H), 2.58( dd, 1H, J=12.5 and 4.5 Hz, H-3"ekv.), 2.23, 2.15, 2.07, 2.05, 2.03, 2.02, 2.0 and 1.84 (singlets, 3H each, CH$_3$CO), 2.06 (s, 6H, 2×CH$_3$CO), 1.67 (t, 1H, J=12.5 Hz, H-3"ax.), 1.01–0.81 (m, 2H, CH$_2$Si), −0.015 (s, (CH$_3$)$_3$Si) ppm.

$^{13}$C-NMR δ: 171.2, 170.9 (2C), 170.8, 170.7, 170.5, 170.1, 170.0, 169.94, 169.88, 168.3 (C-1"), 101.1 (C-1/C-1'), 100.0 (C-1/C-1'), 96.8 (C-2") 76.4, 73.6, 72.5, 72.0, 71.9, 71.4, 70.4, 69.9, 69.3, 67.7, 67.4, 67.3, 66.9, 62.3, 62.2, 61.4, 53.0 (CH$_3$O), 49.0 (C-5"), 37.2 (C-3"), 23.0, 21.3, 20.7–20.4, 17.7 (CH$_2$Si), −1.8 ((CH$_3$)$_3$Si) ppm.

Anal. Calcd. for C$_{49}$H$_{72}$NO$_{29}$Si: C, 50.4; H, 6.2; N, 1.2. Found: C, 50.3; H, 6.4; N, 1.2.

1,2,3.6-Tetra-O-acetyl-4-O-{2,4,6-tri-O-acetyl-3-[methyl (5-acetamido-4,7,8,9, -tetra-O-acetyl-3,5-dideoxy-D-glycero-a-D-galacto-α2-nonulopyranosyl)onate]-β-D-galactopyranosyl}-β-D-glucopyranoside (7)

Compound 6 (840 mg, 0.72 mmol) was dissolved in a mixture of toluene (5.6 mL) and acetic anhydride (1.06 mL). To this solution was added a solution (1.45 mL) of borontrifluoride etherate (0.36 mL, 2.91 mmol) in toluene (2.04 mL). The reaction mixture was stirred for 140 min. and was then worked up by partition between dichloromethane and saturated aqueous sodium hydrogencarbonate. The aqueous phase was extracted once with dichloromethane and the combined organic phases were dried (Na$_2$SO$_4$), filtered and evaporated to give crude (7) (815 mg). Crystallization from methanol gave compound 7 (586 mg). Chromatography (toluene-ethanol 20:1→10:1) of the mother liquor gave additional (7) (154 mg). Total yield of (7) was 740 mg (92%).

According to NMR, compound 7 contained methanol of crystallization in the molar ratio of 0.5 mole methanol per mole of (7). Less than 5% of the 1-α epimer was present as detected by NMR.

[α]D$^{22}$: −0.2° (c 1.9, chloroform)

$^1$H-NMR δ: 5.67 (d, 1H, J=8.5 Hz, H-1), 5.51 (ddd, 1H, J=9.5, 4.5 and 2.5 Hz, H-8"), 5.40 (dd, 1H, J=9.5 and 2.5 Hz, H-7"), 5.22 (t, 1H, J=9H-3), 5.08 (d, 1H, J=10.5 Hz, NH), 5.04 (dd, 1H, J=9.5 and 8.5 Hz, H-2), 4.96–4.83 (3H, H-2', H-4'and H-4"), 4.65 (d, 1H, J=8 Hz, H-1'), 4.50 (dd, 1H, J=10.5 and 3.5 Hz, H-3'), 4.42 (dd, 1H, J=12.5 and 2 Hz, H-9"), 4.42 (dd, 1H, J=12.5 and <2 Hz, H-6/H-6'), 4.20 (dd, 1H, J=12 and 5 Hz, H-9"), 4.08–3.80 (9H), 3.84 (s, CH$_3$O), 3.75 (ddd, 1H, J=10.5 and 2 Hz, H-5/H-5'), 3.62 (dd, 1H, J=11 and 3 Hz, H-6/H-6'), 3.45 (d, 1.5H, J=5.5 Hz, CH$_3$OH), 2.57 (dd, 1H, J=12.5 and 5 Hz, H-3"ekv.), 2.24–1.83 (CH$_3$CO signals), 1.67 (t, 1H, J=12.5 Hz, H-3"ax.), 1.09 (q, 0.5H, J=5.5 Hz, (CH$_3$OH) ppm.

$^{13}$C-NMR (measured on chromatographed, methanol free material) δ: 171.2, 170.9, 170.7, 170.66, 170.61, 170.5, 169.94, 169.9, 169.8, 169.2, 168.2, 101.0 (C-1'), 96.8 (C-2"), 91.6 (C-1), 75.7, 73.5, 73.1, 71.9, 71.3, 70.6, 70.4, 69.8, 69.2, 67.7, 67.2, 66.7, 62.0, 61.8, 61.5, 53.2 (CH$_3$O), 49.0 (C-5"), 37.2 (C-3"), 22.9, 21.3, 20.7, 20.6, 20.5, 20.5, 20.4 ppm.

3-Bromo-2-bromomethylprop-1-yl 2,3,6-tri-O-acetyl-4-O-{2,4,6-tri-O-acetyl-3-O-[methyl (5-acetamido-4,7,8,9-tetra-O-acetyl-3,5-dideoxy-D-glycero-α-D-galacto-2-nonulopyranosyl)onate]-β-D-galactopyranosyl}-β-D-glucopyranoside (8)

Compound 7 (0.96 g, 0.86 mmol) and 3-bromo-2-bromomethylpropan-1-ol (Ansari et al., 1987) (1.5 g, 6.5 mmol) were dissolved in dry dichloromethane (30 mL) and was then cooled to 0° C. Borontrifluoride etherate (1.9 mL, 15 mmol) was added and the mixture was stirred at 0° C. for 40 min. The cooling bath was removed and stirring was continued for 5 h. The mixture was then diluted with dichloromethane and washed with ice-cold saturated aqueous sodium hydrogencarbonate. The dichloromethane phase was dried (Na$_2$SO$_4$), filtered and evaporated. Chromatography (toluene-ethanol, 20:1→12:1) gave amorphous compound 8 (512 mg, 46%).

[αD$^{22}$: −0.5 (c 2.6, chloroform)

$^1$H-NMR δ: 5.54 (ddd, 1H, J=9.5, 5 and 2.5 Hz, H-8"), 5.40 (dd, 1H, J=9.5 and 3 Hz, H-7"), 5.19 (t, 1H, J=9.5 Hz, H-3), 5.04 (d, 1H, J=10 NH), 4.97–4.82 (4H), 4.67 (d, 1H, J=8 Hz, h-1'), 4.54–4.37 (4H), 4.19 (dd, 1H, J=12 and 5.5 Hz, H-9"), 4.10–3.80 (10H), 3.84 (s, CH$_3$O), 3.66–342 (8H), 2.58 (dd, 1H, J=12.5 and 4.5 Hz, H-3 ekv.), 2.38–2.22 (m, CH(CH$_2$Br)$_2$), 2.24 (s, 3H), 2.16 (s, 3H), 2.10 (s, 3H), 2.08 (s, 6H), 2.07 (s, 3H), 2.06 (s, 6H), 2.04 (s, 3H), 2.00 (s, 3H), 1.85 (s, 3H), 1.68 (t, 1H, J=12.5 Hz, H-3"ax.) ppm.

$^{13}$C-NMR δ: 171.1, 170.94, 170.9, 170.7, 170.6, 170.6, 170.5, 170.0, 169,97, 169.7, 169.8, 166.2 (C-1"), 101.1, 100.8, 96.8 (C-2"), 76.2, 73.1, 72.7, 72.0, 71.6, 71.3, 70.4, 69.6, 69.2, 69.1, 67.7, 67.2, 66.8, 62.1, 61.4, 53.0 (CH$_3$O), 47.0 (C-5"), 42.4 (CH(CH$_2$Br)$_2$), 37.2 (C-3"), 32.7 (CH$_2$Br), 31.6 (CH$_2$Br), 22.9, 21.3, 20.7, 20.5, 20.4, 20.4 ppm.

3-Bromo-2-bromomethylpropyl 4-O-{3-O-[sodium (5-acetamido-3,5-dideoxy-D-glycero-α-D-galacto-2-nonulopyranosyl)onate]-β-D-glactopyranosyl}-β-D-glucopyranoside (9)

Compound 8 (384 mg, 0.30 mmol) was dissolved in methanolic sodium methoxide (0.03M, 60 mL) and stirred over night. Water (100 μL) was added and the mixture was neutralized with silica, filtered and concentrated. Chromatography (chloroform-methanol-water, 65:53:6) gave amorphous compound 9 (189 mg, 74%).

[β]D$^{22}$: −3.4° (c 0.3, methanol)

$^1$H-NMR (CD$_3$OD) δ: 4.44 (d, 1H, J=8 Hz, H-1/H-1'), 4.31 (d, 1H, J=8 Hz, H-1/H-1'), 2.86 (dd, 1H, J=12.5 and 3.5 Hz, H-3"ekv., virtually coupled), 3.43–2.31 (m, 1H, CH(CH$_2$Br)$_2$), 2.02 (s, 3H, NCOCH$_3$), 1.73 (bt, 1H, J=12.5 Hz, H-3"ax., virtually coupled) ppm.

$^{13}$C-NMR (CD$_3$OD) δ: 175.5, 174.9, 105.1(C-1/C-1'), 104.6(C-1/C-1'), 101.1 (C-2"), 54.0 (C-5"), 44.4 (CH(CH$_2$Br)$_2$), 42.1 (C-3"), 33.9 (CH$_2$Br), 33.7 (CH$_2$Br), 22.7 (NCOCH$_3$) ppm.

2-Bromoethyl 4-O-βD-galactopyranosyl-β3-D-glucopyranoside (11)

2-Bromoethyl 4-O-(2,3,4,6-tetra-O-acetyl-β-D-galactopyranosyl)-2,3,6-tri-O-acetyl-β-D-glucopyranoside (0.17 mol) was prepared according to Dahmén et aL (1983 b). The crude product was dissolved in methanolic sodium methoxide (0.01M, 1 L) and stirred for 3 h. The mixture was neutralized with silica, filtered and concentrated. Chromatography (dichloromethane-methanol-water, 65:20:3) and crystallisation from ethanol gave compound 11 (37 g, 51%). m.p. 151°–152° C.

$^1$H-NMR (D$_2$O,acetone) δ: 4.57 (d, 1H, J=8.0 Hz, H-1), 4.45 (d, 1H, J=8 Hz, H-1'), 4,26–4.19 (m, 1H, OCH$_2$CH$_2$Br), 3.98 (dd, 1H, J=12.5 and 1 Hz, H-6/H-6'), 3.93 (d, 1H, J=3.5 Hz, H-4'), 3.55 (dd, 1H, J=10 and 8 Hz H-2'), 3.40–3.30 (m, 1H, H-2) ppm.

$^{13}$C-NMR (D$_2$O, acetone) δ: 105.7 (C-1'), 104.9 (C-1), 75.5 (C-2'), 73.7 (C-2), 71.3 (C-4'), 63.8 (C-6/C-6'), 62.9 (C-6/C-6'), 33.9 (CH$_2$Br) ppm.

2-Bromoethyl 4-O-(3,4-O-isopropylidene-β-D-galactopyranosyl)-βglucopyranoside (12)

A mixture of compound 11 (35 g, 78 mmol) and p-toluenesulfonic acid (1.5 g, 8 mmol) in 2,2-dimethoxypropan (800 mL) was stirred at 50° for 1 h and then at room temperature over night. Triethylamine (12 mL, 80 mmol) was added and the mixture was stirred for 30 min, concentrated and evaporated with toluene to remove excess triethylamine. The crude product was dissolved in methanol-water (10:1, 900 mL) and boiled under reflux for 2 h. Saturated aqueous sodium hydrogencarbonate (20 mL) was added and the mixture was concentrated. Flash chromatogaraphy (chloroform-methanol-triethylamine, 10:1:0.01) and crystallisation from ethanol gave compound 12 (32.7 g, 86%).

m.p. 171°–172° C.

[α]D$^{22}$: +11.1 (c 0.7, methanol).

$^1$H-NMR (D$_2$O, acetone) δ: 4.56 (d, 1H, J=8 Hz, H-1), 4.49 (d, 1H, J=8.5 Hz, H-1'), 4.37 (dd, 1H, J=5.5 and 1.5 Hz, H-4'), 3.51 (dd, 1H, J=8 and 8.0 Hz, H-2'), 3.36 (dd,1H, J=9.0 and 8 Hz, H-2), 1.55 (s, 3H, CH$_3$), 1.40 (s, 3H, CH$_3$) ppm.

$^{13}$C-NMR (D$_2$O, acetone) δ: 113.7 ((CH$_3$)$_2$C), 104.9 (C-1/C-1'), 81.4 (C-5), 81.3 (C-3'), 77.5 (CH$_2$CH$_2$Br), 77.0 (C-3), 76.5 (C-4'), 76.2 (C-5'), 75.5 (C-2/C-2'), 63.5 (C-6/C-6'), 62.6 (C-6/C-6'), 33.8 (CH$_2$CH$_2$Br),29.9 (CH$_3$C), 28.1 (CH$_3$C) ppm.

Anal. Calc. for C$_{17}$H$_{29}$BrO$_{11}$: C, 41.7;H, 6.0. Found: C, 41.5;H, 6.0.

2-Bromoethyl 2.6-di-O-benzoyl-4-(6-O-benzoyl-β-D-galactopyranosyl)-β-D-glucopyranoside (13)

Compound 12 (9.0 g, 18.4 mmol) was dissolved in a mixture of dry pyridine (60 mL) and dichloromethane (150 mL) and cooled to –50° C. Benzoylchloride (10.5 mL, 90.6 mmol) in dry dichloromethane (150 mL) was added dropwise during 3 h and the mixture was stirred for additional 1 h. Methanol was then added and the solution was concentrated. The residue was dissolved in dichloromethane (500 mL) and washed with aqueous hydrogen chloride (2M, 250 mL), saturated aqueous sodium hydrogencarbonate (250 mL), saturated aqueous sodium chloride (250 mL), dried (Na$_2$SO$_4$) and concentrated. The crude product was dissolved in 80% aqueous acetic acid (250 ml), stirred at 80° C. for 30 min. and then concentrated. Chromatography (dichloromethane-methanol, 30:1) gave amorphous compound 13 (4.3 g, 31%).

[α]D$^{22}$: +15.8° (c 1.0, chloroform).

$^1$H-NMR δ: 8.24–8.02 (m,15H, Ar-H), 5.19 (dd, 1H, J=9.5 and 8 Hz, H-2), 4.84 (dd, $_1$H, J=12.0 and 1.5 Hz, H-6 /H-6'), 4.66 (dd, 1H, J=12 and 3.5 Hz, H-6/H-6'), 4.64 (d, 1H, J=8 Hz, H-1), 4.48 (dd, 1H, J=12.0 and 6 Hz, H-6/H-6'), 4.37 (dd, 1H, J=12 and 9 Hz, H-6/H-6'), 4.35 (d, 1H, J=8 Hz, H-1') ppm.

$^{13}$C-NMR δ: 166.8, 166.6, 165.5, 104.1 (C-1'), 101.0 (C-1), 81.7, 73.5, 73.2, 73.1, 73.02, 72.96, 70.8, 69.6, 68.9, 64.1 (C-6/C-6'), 63.9 (C-6/6'), 29.6 (OCH$_2$CH$_2$Br) ppm.

Anal. Calc. for C$_{35}$H$_{37}$BrO$_{14}$: C, 55.2; H, 4.9. Found: C, 55.2; H, 4.9.

2-Bromoethyl 2,6-di-O-benzoyl-4-O-{6-O-benzoyl-3-O-[methyl(5-acetamido-4,7,8,9-tetra-O-acetyl-3,5-dideoxy-D-glycero-α-D-galacto-2-nonulopyranosyl)onate]-β-D-galactopyranosyl}-β-D-glucopyranoside (14)

Compound 13 (200 mg, 0.26 mmol), 5 (263 mg, 0.44 mmol) and powdered molecular sieves (3A, 300 mg) in a mixture of acetonitrile and dichloromethane (9:4, 8 mL) was stirred for 1 h under argon. Silver trifluoromethanesulfonate (118 mg, 0.45 mmol) was added and the reaction mixture was cooled to –60° C. Methylsulfenyl bromide (Dasgupta and Garegg, 1988) in dichloromethane (3.48M, 126 μL, 0.44 mmol) was added dropwise during 5 min. and the mixture was then stirred for 1 h. Diisopropylamine (0.7 mL, 2.6 mmol) was added and stirring was continued for 0.5 h. The mixture was allowed to attain 0° C., filtered and concentrated. Chromatography (chloroform-methanol, 50:1) gave amorphous compound 14 (244 mg, 75%).

[α]D$^{22}$: +14.9° (c 1.0, chloroform)

$^1$H-NMR δ: 5.33 (m, 1H, H-8"), 5.28 (dd, 1H, J=8.0 Hz, H-7"), 5.26 (dd, 1H, J=9.5 Hz, H-2), 5.03–4.93 (m, 2H, H-4", H-6/H-6'), 4.74 (dd, 1H, J=12 and 3.5 Hz, H-6/H-6'), 4.70 (d, 1H, J=8 Hz, H-1), 4.59 (d, 1H, J=8 Hz, H-1'), 4.50 (dd, 1H, J=12 and 6 Hz, H-6/H-6'), 2.70 (dd, 1H, J=13.0 and 4.5 Hz, H-3"ekv.) ppm. (H-3,H-2'and H-4' were shifted downfield after acetylation of 14)

$^{13}$C-NMR δ: 170.7, 170.4, 170.3, 170.1, 170.1, 168.1 (C-1", JC-1"-H-3"ax=6.1 Hz), 166.6, 166.1, 165.4, 104.4 C-1'), 101.1 (C-1), 97.6 (C-2"), 82.2, 76.4, 73.4, 73.0, 72.9, 63.7, 63.4, 62.4 (C-6, C-6', C-6"), 53.2 (CH$_3$O), 49.6 (C-5"), 37.6 (C-3"), 29.6 (OCH$_2$CH$_2$Br), 23.1 (NCOCH$_3$), 21.0, 20.7, 20.6, 20.5 ppm.

Anal. Calc for C$_{55}$H$_{64}$BrNO$_{26}$: C, 53.5;H, 5.2. Found: C, 53.5;H, 5.5.

2-Bromoethyl 4-O-{3-O-[sodium (5-acetamido-3,5-dideoxy-D-glycero-α-D-galacto-2-nonulopyranosyl)onate]-β-D-galactopyranosyl}-βD-glucopyranoside (15)

Compound 14 (200 mg, 0.16 mmol) was dissolved in methanolic sodium methoxide (0.03M, 50 mL) and stirred for 6 h. Water (50 μL) was added and the mixture was stirred for 5 min., neutralized with silica, filtered and concentrated. Chromatography (chloroform-methanol-water, 6:4:1) gave amorphous compound 15 (118 mg, 96%).

[α]D$^{22}$: –0.9 (c 1.0, water)

$^1$H-NMR (D$_2$O, acetone) δ: 4.57 (d, 1H, J=8 Hz, H-1/H-1'), 4.54 (d, 1H, J 8.5 Hz, H-1 or H-1'), 2.77 (dd, 1H, J 12.2 and 4.3 Hz, H-3e", 2.03 (s, 3H, NCOCH$_3$), 1.81 (bt, 1H, H-3a").

$^{13}$C-NMR (D$_2$O, acetone) δ: 177.0, 176.7, 105.6 (C-1'), 105.1 (C-1), 102.8 (C-2"), 54.7 (C-5"), 42.7 (C-3"), 34.0 (OCH$_2$CH$_2$Br), 25.0 (NCOCH$_3$) ppm.

2-bromoethyl 4-O-(α-D-galactopyranosyl)-β-D-galactopryranoside (28)

2-Bromoethyl 2,3,6-tri-O-acetyl-4-O-(2,3,4,6-tetra-O-acetyl-α-D-galactopyranosyl-β-D-galactopyranoside (27) (Dahmén et al. (1983 a) p. 116) was prepared by boron trifluoride etherate catalyzed glycosidation of the corresponding octaacetate (Dahmén et al. (1983 a) p. 113) (1.25 g, anomeric mixture). The crude product was suspended in methanol (20 mL) and methanolic sodium methoxide (0.2M, 4 mL) was added. A clear solution was obtained after 30 min. The reaction mixture was stirred for additional 30 min. and was then neutralized using silica. Filtration, evaporation and chromatography (chloroform-methanol-water; 65:35:6) gave compound 28 (335 mg, 41%).

$[\alpha]D^{22}$: +69° (c 1.0, methanol)

1 H-NMR (CD$_3$OD) δ: inter alia 4.76 (d, 1H, J=2 Hz, H-1'), 4.15 (d, 1H, J=7 Hz, H-1'), 4.09 (bt, 1H, J=6 Hz), 3.92 (dt, J=11.5 and 6.5 Hz) ppm.

$^{13}$C-NMR (CD$_3$OD) δ: 105.2, 102.5, 79.2, 76.2, 74.6, 72.7, 71.3, 71.1, 70.7, 62.7, 61.1, 30.9 ppm.

$^{13}$C-NMR (D$_2$O, ref. acetone at 33.19 ppm): δ: 105.9, 103.2, 80.0, 78.1, 75.2, 73.8, 73.7, 73.1, 72.1, 72,0, 71.6, 63.5, 63.0, 34.1 ppm.

Anal. Calc. for C$_{14}$H$_{25}$BrO$_{11}$: C, 37.4; H, 5.6. Found: C, 37.1; H, 59.

2-Bromoethyl 4-O-(4-O-α-D-galactopyranosyl-β-D-galactopyranosyl)β-D-glucopyranoside (48)

2-Bromoethyl 2,3,6-tri-O-acetyl-4-O-[2,3,6-tri-O-acetyl-4-O-(2,3,4,6-tetra-o-acetyl-α-D-galactopyranosyl)-β-D-galactopyransosyl)]-β-D-glucopyranoside (53) (Dahmen et al. 1984) 35 mg) was deacetylated by stirring in 10 mL of 0.1M methanolic sodium methoxide for 16 h. Neutralization using silica gel, filtration, evaporation and chromatography (chloroform-methanol-water; 65:35:6) followed by microfiltration and lyophilization gave 48 (18.6 mg, 90%)

$[\alpha]D^{22}$: +51° (c 1.0, water)

$^1$H-NMR (D$_2$O, ref. acetone at 2.24 ppm) δ: 4.96 (d, 1H, J=4 Hz, H-1"), 4.57 (d, 1H, J=8.0 Hz, H-1/H-1'), 4.52 (d, 1H, J=7.5 Hz, H-1/H-1), 4.37 (bt, 1H) 4.27–4.19 (m, 1H, CH$_2$CH$_2$Br) 4.09–3.55 (19H), 3.36 (bt, 1H) ppm $^{13}$C-NMR (D$_2$O, ref. acetone at 33.19 ppm) δ: 106.2 (C-1/C-1), 105 1 (C-1/C-1'), 103.3 (C-1"), 81.6, 80.3, 78.4, 77.8, 77.3, 75.7, 75.1, 73.9, 73.8, 73.0, 72.1, 71.9, 71.5, 63.5, 63.3, 63.0, 33.9 (CH$_2$Br) ppm.

2-Bromoethyl glycoside of "GM$_3$ Lactam" (55)

The corresponding decaacetate of the title compound (Ray et al. 1992) (40 mg, 1α/1β1:2.2) was de-O-acetylated in 9.5 mM methanolic sodium methoxide at room temperature for 7 h. Neutralization with silica gel, evaporation and chromatography (chloroform-methanol-water, 65:35:6) gave 55 (26 mg. quant.).

1H-NMR (D$_2$O,(CH$_3$)$_3$Si(CD$_2$)$_2$COONa) δ: inter alia 3.37 (bt, 1H), 2.61 (dd, 1H, J=13 and 6 Hz, H-3"e), 2.05 (s, 3H, NCOCH$_3$), 1.71 (dd, 1H, J=11 and 13 Hz, H-3"a) ppm.

The peptides O-glycosylated at serine side chain were synthesised using solid phase peptide synthesis technique. Glycosylation of serine (protected as a 9-fluorenylmethoxycarbonyl- and pentafluorophenyl derivative at the amino- and carboxy groups respectively) with O-acylated β-thioglycosicles of Galα4Gal gave O-glycosylated serine derivatives. These derivatives were used in solid phase peptide synthesis. After cleavage from the resin and purification by HPLC, glycopeptides were obtained which were still protected at the carbohydrate moiety as acyl derivatives. Complete de-protections were performed using base catalysis, and the products purified by HPLC. FAB-MS data of the products were in agreement with theoretical values.

TABLE 1A

| SEQ ID NO: Peptides used for conjugation are: | | Comp No. | |
|---|---|---|---|
| 4 | K I A S N E N M D A M E S S T L E C | (16) | (D$^b$-restricted) |
| 5 | K I A S N E N M E T M E | (17) | (D$^b$-restricted) |
| 6 | K A S N E N M E T M C | (18) | (D$^b$-restricted) |
| 7 | C A S N E N M E T M | (19) | (D$^b$-restricted) |
| 8 | C S G P S N T P P E I | (20) | (D$^b$-restricted) |
| 9 | S G V E N P G G Y C L T | (26) | (D$^b$-restricted) |
| 21 | A S N E N h E T M | (32) | (D$^b$-restricted) |
| 22 | A S N h N M E T M | (33) | (D$^b$-restricted) |
| 23 | S G P S N h P P E I | (34) | (D$^b$-restricted) |
| 24 | S G P h N T P P E I | (35) | (D$^b$-restricted) |
| 13 | C R G Y V Y Q G L | (36) | (K$^b$-restricted) |
| 14 | C A P G N Y P A L | (37) | (K$^b$-restricted) |
| 25 | R G Y h Y Q G L | (38) | (K$^b$-restricted) |
| 26 | F A P G h Y P A L | (39) | (K$^b$-restricted) |
| SEQ ID NO: Other examples of peptides suitable for conjugation are: | | | |
| 10 | K Q I A S N E N M E T M E S C | | (D$^b$-restricted) |
| 11 | K G P S N T P P E I C | | (D$^b$-restricted) |
| 12 | K S G P S N T P P E I H C | | (D$^b$-restricted) |
| 3 | G I L G F V F T L | | (HLA-A2-restricted) |
| 15 | M V V K L G E F Y N Q M M | | (HLA-A2-restricted) |
| 16 | C P T N Q Q V V L E G T N K T D | | (HLA-A2-restricted) |
| 17 | M Q I R G F V Y F V E T | | (HLA-A2-restricted) |
| 18 | L S P G M M M G M F N M | | (HLA-A2-restricted) |

(h = homocysteine)

Methods used for the preparation of glycopeptides

Method A: Conjugation via 2-bromomethylprop-2-en-1-yl spacer

A slurry of the 3-bromo-2-bromomethylprop-1-yl glycoside (10 μmol) and N,N,N,N-tetrabutylammonium fluoride (40–100 μmol) in N,N-dimethylformamide (100 μL) was stirred for 10 min. under argon. The peptide (8 μmol) dissolved in N,N-dimethylformamide (DMF) or dimethylsulfoxide (DMSO) (200–1000 μL) was added and the mixture was sonicated for 5 min. and then stirred for 1.5–2.5 h. The reaction was monitored by HPLC. The mixture was diluted with 0.1% aqueous trifluoroacetic acid and lyophilized. Preparative HPLC (acetonitrile-water-0.1% trifluoroacetic acid) gave the expected glycopeptides (see Table 2).

Method B: Conjugation via 2-bromoethyl spacer

The peptide (5 μmol) was added to a slurry of the 2-bromoethyl glycoside (10 μmol) and cesium carbonate (20–100 μmol) in N,N-dimethylformamide (400 μL) under argon. The mixture was sonicated for 5 min. and then stirred for 1–5 h. The reaction was monitored by HPLC, diluted with 0.1% aqueous trifluoroacetic acid and lyophilized. Preparative HPLC (acetonitrile-water-0.1% trifluoroacetic acid) gave the expected glycopepticles (see Table 2).

The peptides and the synthesized glycopeptides are present as trifluoromethanesulfonate salts.

In addition to the method using cesium carbonate as a promoter, the peptide conjugate 24 was also prepared according to the method of Or et al, HPLC analyses of both the reaction mixtures revealed a major product peak having the same retention time. However, a cleaner reaction and a more easily purified product was obtained with cesium carbonate as a promoter.

Preparation of glycopeptides, examples

Conjugate 21

A slurry of 9 (2.9 mg, 3.4 μmol) and N,N,N,N-tetrabutylammonium fluoride (9.8 mg, 30.6 μmol) in N,N-dimethylformamide (35 μL) was stirred for 10 min. under argon. Peptide 16 (8.1 mg, 2.7 μmol) dissolved in dimethylsulfoxide (350 μL) was added and the mixture was sonicated for 5 min and then stirred for 1.5 h. The reaction was monitored by HPLC (gradient from 0 to 40% acetonitrile in 0.1% aqueous trifluoroacetic acid, 20 min). The mixture was diluted with 0.1% aqueous trifluoroacetic acid and lyophilized. Preparative HPLC (17% acetonitrile in 0.1% aqueous trifluoroacetic acid) gave compound 21 (1 mg, 11%).

Retention times (analytical runs): Allylic bromide (from 9): 10.7 min.; 21; 14.2 min.; 16: 15.8 min.

Conjugate 22

A slurry of 9 (11 mg, 12.9 μmol) and N,N,N,N-tetrabutylammonium fluoride (37 mg, 116 μmol) in N,N-dimethylformamide (130 μL) was stirred for 10 min under argon. Peptide 17 (20 mg, 10.2 μmol) dissolved in dimethylsulfoxide (750 μL) was added and the mixture was sonicated for 5 min and then stirred for 2.5 h. The reaction was monitored by HPLC (gradient from 0 to 40% acetonitrile in 0.1% aqueous trifluoroacetic acid, 20 min). The mixture was diluted with 0.1% aqueous trifluoroacetic acid, and lyophilized. Preparative HPLC (14% acetonitrile in 0.1% aqueous trifluoroacetic acid) gave compound 22 (3 mg, 10%).

Retention times (analytical runs): Allylic bromide (from 9): 10.7 min.; 22: 13.0 min.; 17: 14.3 min.

Conjugate 23

Compound 9 (13 mg, 15.5 μmol) was treated with N,N,N,N-tetrabutylammonium fluoride (39 mg, 124.0 μmol) in N,N-dimethylforrnamide (150 μL) and peptide 18 (20 mg, 12.0 μmol) in dimethylsulfoxide (600 μL) was added and the mixture was sonicated for 5 min and then stirred for 2.5 h. The reaction was monitored by HPLC (gradient from 0 to 40% acetonitrile in 0.1% aqueous trifluroacetic acid, 20 min). The mixture was diluted with 0.1% aqueous trifluoroacetic acid and lyophilized. Preparative HPLC (12% acetonitrile in 0.1% aqueous trifluoroacetic acid) gave compound 23 (8 mg, 29%).

Retention times (analytical runs): 23: 12.2 min; 18: 13.5 min

Conjugate 24

Peptide 19 (10 mg, 6.8 μmol) was added to a slurry of compound 15 (10 mg, 13.6 μmol) and cesium carbonate (11.5 mg, 35.2 μmol) in N,N-dimethylformamide (550 μL) under argon. The mixture was sonicated for 5 min and then stirred for 5 h. The reaction was monitored by HPLC (gradient from 0 to 30% acetonitrile in 0.1% aqueous trifluoroacetic acid, 30 min). The mixture was diluted with 0.1% aqueous trifluoroacetic acid and lyophilized. Preparative HPLC (gradient from 12 to 15% acetonitrile in 0.1% aqueous trifluoroacetic acid, 30 min) gave 24 (8.5 mg, 59%).

Retention times (analytical runs): 15: 8.7 min; 24: 18 min; 19: 19.3 min.

Preparation of conjugate 24 according to the method of Or et al. (1991):

Compound 15 (8 mg, 10.5 μmol) and peptide 19 (2 mg, 1.4 μmol) were dissolved in dry N,N-dimethylformamide (400 μL) under argon. The solution was saturated with ammonia and stirred for 1.5 h. The reaction was monitored by HPLC (gradient from 0 to 30% acetonitrile in 0.1% aqueous trifluoroacetic acid, 30 min) and showed a major peak (52%) with the same retention time (18 min) as compound 24 prepared according to method B.

Conjugate 25

Peptide 20 (10 mg, 6.0 μmol) was added to a slurry of compound 15 (9 mg, 12.0 μmol) and cesium carbonate (39 mg, 120 μmol) in N,N-demethylformamide (500 μL) under argon. The mixture was sonicated for 5 min and then stirred for 1 h. The reaction was monitored by HPLC (gradient from 0 to 30% acetonitrile in 0.1% aqueous trifluoroacetic acid, 30 min) The mixture was diluted with 0.1% aqueous trifluoroacetic acid and lyophilized. Preparative HPLC (gradient from 13 to 18% acetonitrile in 0.1% aqueous trifluoroacetic acid, 30 min) gave compound 25 (14 mg, 60%).

Retention times (analytical runs): 15: 8.7 min; 25: 20.5 min; 20: 21.7 min.

Conjugate 29

The peptide 20 (20.5 mg, 12.3 μmol) was added to a slurry of compound 28 (31.6 mg, 70.3 μmol) and cesium carbonate (110.3 mg, 338 μmol) in N,N-dimethylformamide (1.6 mL) under argon. The mixture was sonicated for 5 min. and then stirred for 3 h. The reaction was monitored by HPLC (gradient from 0 to 30% acetonitrile in 0.1% aqueous trifluoroacetic acid, 30 min), diluted with 0.1% aqueous trifluoroacetic acid and lyophilized. Preparative HPLC (gradient from 13 to 18% acetonitrile in 0.1% aqueous trifluoroacetic acid, 30 min) gave compound 29 (17.6 mg, 70%).

Retention times (analytical runs): 28: 6.2 min, 29: 20.8 min, 20: 21.8 min.

Conjugate 30

Peptide 26 (10 mg, 6.5 μmol) was dissolved in N,N-dimethylformamide (800 mL) under argon. Compound 28 (11.7 mg, 26 μmol) and cesium carbonate (21.2 mg, 65 μmol) were added. The mixture was sonicated for 5 min and then stirred for 2 h. The reaction was monitored by HPLC (gradient from 0 to 30% acetonitrile in 0.1% aqueous trifluoroacetic acid, 30 min). The mixture was diluted with 0.1% aqueous trifluoroacetic acid and lyophilized. Preparative HPLC (gradient from 13 to 18% acetonitrile in 0.1% aqueous trifluoroacetic acid, 30 min) gave compound 30 (11.2 mg, 90%).

Retention times (analytical runs, gradient from 0 to 30% acetonitrile in 0.1% aqueous trifluoroacetic acid, 50 min): 28: 6.2 min, 30: 21.5 min, 26: 24.4 min.

Conjugate 31

Peptide 19 (15 mg, 10 μmol) was dissolved in N,N-dimethyl formamide (1.2 mL) under argon. Compound 28 (18 mg, 40 μmol) and cesium carbonate (76.2 mg, 234 μmol) was added. The mixture was sonicated for 5 min and then stirred for 3 h. The reaction was monitored by HPLC (gradient from 0 to 30% acetonitrile in 0.1% aqueous trifluoroacetic acid, 30 min). The mixture was diluted with 0.1% aqueous trifluoroacetic acid and lyophilized. Preparative HPLC (gradient from 13 to 18% acetonitrile in 0.1% aqueous trifluoroacetic acid, 30 min) gave compound 31 (13.8 mg, 75%).

Retention times (analytical runs): 28: 6.2 min, 31: 17.7 min, 19: 19.1 min.

Conjugate 40

Peptide 38 (10 mg, 7.6 μmol) was dissolved in N,N-dimethyl-formamide (0.8 mL) under Argon. Compound 28 (13.7 mg, 30.5 μmol) and cesium carbonate (24.8 mg, 76 μmol) was added. The mixture was sonicated for 30 min and then stirred for 1 h. The reaction was monitored by HPLC (gradient from 0 to 40% acetonitrile in 0.1% aqueous trifluoroacetic acid, 30 min). The mixture was diluted with 0.1% aqueous trifluoroacetic acid (16 mL) and lyophilized. Preparative HPLC (gradient from 16 to :21% acetonitrile in 0.1% aqueous trifluoroacetic acid, 30 min) gave 40 (16.6 mg, 52%).

Retention times (analytical runs): 28: 6.7 min, 40: 18.8 min, 38: 21 min.

Conjugate 41

Peptide 39 (10 mg, 8 μmol) was dissolved in N,N-dimethylformamide (0.8 mL) under Argon. Compound 28 (14.3 mg, 32 μmol) and cesium carbonate (27.6 mg, 85 μmol) was added. The mixture was sonicated for 15 min and then stirred for 65 min. The reaction was monitored by HPLC (gradient from 0 to 40% acetonitrile in 0.1% aqueous trifluoroacetic acid, 30 min). The mixture was diluted with 0.1% aqueous trifluoroacetic acid (16 mL) and lyophilized. The crude product was pooled with two additional batches prepared analogously from 5 and 6 mg of peptide respectively. Preparative HPLC of the pooled material (gradient from 19 to 24% acetonitrile in 0.1% aqueous trifluoroacetic acid, 30 min) gave 41 (23.7 mg, 85%).

Retention time (analytical runs): 28: 6.7 min, 41: 22.2 min, 39: 24.3 min.

Conjugate 42

Peptide 36 (5 mg, 3.6 μmol) was dissolved in N,N-dimethyl-formamide (0.4 mL) under Argon. Compound 28 (6.4 mg, 14.3 μmol) and cesium carbonate (11.6 mg. 35.7 μmol) was added. The mixture was sonicated for 5 min and then stirred for 2 h. The reaction was monitored by HPLC (gradient from 17 to 22% acetonitrile in 0.1% aqueous trifluoroacetic acid, 30 min). The mixture was diluted with 0.1% aqueous trifluoroacetic acid (8 mL) and lyophilized. Preparative HPLC (gradient from 17 to 22% acetonitrile in 0.1% aqueous trifluoroacetic acid, 30 min) gave 42 (7.1 mg, 95%, purity: 85%).

Retention times (analytical runs): 28: 6.2 min, 42: 26.4 min, 36: 27.6 min.

Conjugate 43

Peptide 37 (10 mg, 7.35 μmol) was dissolved in N,N-dimethyl-formide (0.8 mL) under Argon. Compound 28 (13.2 mg, 29.4 μmol) and cesium carbonate (23.9 mg, 73.4 μmol) was added. The mixture was monitored by HPLC (gradient from 5 to 35% acetonitrile in 0.1% aqueous trifluoroacetic acid, 30 min). The mixture was diluted with 0.1% aqueous trifluoroacetic acid (16 mL) and lyophilized. Preparative HPLC (gradient from 17 to 22% acetonitrile in 0.1% aqueous trifluoroacetic acid, 30 min) gave 43 (93 mg, 73%).

Retention times (analytical runs): 28: 6.2 min, 43: 24.6 min, 37: 25.9 min.

Conjugate 44

Peptide 32 (10 mg, 8 μmol) was dissolved in dimethylsulfoxide (0.8 mL) under Argon. Compound 28 (14.5 mg, 32 μmol) was cesium carbonate (26 mg, 80 μmol) was added. The mixture was sonicated for 10 min and then stirred for 1 h. The reaction was monitored by HPLC (gradient from 0 to 30% acetonitrile in 0.1% aqueous trifluoroacetic acid, 30 min). The mixture was diluted with 0.1% aqueous trifluoroacetic acid (16 mL) and lyophilized. The crude product was pooled with an additional batch prepared analogously from 10 mg of peptide. Preparative HPLC of the pooled material (gradient from 7 to 12% acetonitrile in 0.1% aqueous trifluoroacetic acid, 30 min) gave 44 (14 mg, 54%).

Retention times (analytical runs): 28: 6.2 min, 42: 14.6 min, 32: 16.8 min.

Conjugate 45

Peptide 34 (10 mg, 6.8 mol) was dissolved in N,N-dimethyl-formamide (0.8 mL) under Argon. Compound 28 (11.2 mg, 25 μmol) and cesium carbonate (20.2 mg, 62 mol) was added. The mixture was sonicated for 10 min and then stirred for 2 h. The reaction was monitored by HPLC (gradient from 0 to 30% acetonitrile in 0.1% aqueous trifluoroacetic acid, 30 min). The mixture was diluted with 0.1% aqueous trifluoroacetic acid (16 mL) and lyophilized. Preparative HPLC (gradient from 13 to 18% acetonitrile in 0.1% aqueous trifluoroacetic acid, 30 min) gave 45 (7.9 mg, 63%).

Retention times (analytical runs): 28: 6.2 min, 45: 20.5 min, 34: 25.2 min.

Conjugate 46

Peptide 35 (10 mg, 6.7 μmol) was dissolved in N,N-dimethylformamide (0.8 mL) under Argon. Compound 28 (12.1 mg, 27 μmol) and cesium carbonate (43.7 mg. 134 mol) was added. The mixture was sonicated for 20 min and then stirred for 4 h. The reaction was monitored by HPLC (gradient from 0 to 30% acetonitrile in 0.1% aqueous trifluoroacetic acid, 30 min). The mixture was diluted with 0.1% aqueous trifluoroacetic acid (16 mL) and lyophilized. Preparative HPLC (gradient from 13 to 18% acetonitrile in 0.1% aqueous trifluoroacetic acid, 30 min) gave 46 (17.4 mg, 56%).

Retention times (analytical runs): 28: 6.2 min, 46: 21.0 min, 35: 23.8 min.

Conjugate 47

Peptide 33 (10 mg, 8 μmol) was dissolved in dimethylsulfoxide (0.8 mL) under Argon. Compound 28 (14.5 mg, 32 μmol) and cesium carbonate (26 mg, 80 μmol) was added. The mixture was sonicated for 10 min and then stirred for 1 h 55 min. The reaction was monitored by HPLC (gradient from 0 to 30% acetonitrile in 0.1% aqueous trifluoroacetic acid, 30 min). The mixture was diluted with 0.1% aqueous trifluoroacetic acid (16 mL) and lyophilized. The crude product was pooled with two additional batches prepared analogously from 5 and 10 mg of peptide respectively. Preparative HPLC of the pooled material (gradient from 10 to 15% acetonitrile in 0.1% aqueous trifluoroacetic acid, 30 min) gave 47 (18.9 mg, 59%).

Retention times (analytical runs): 28: 6.2 min, 47: 18.3 min, 33: 20.6 min.

Conjugate 49

Peptide 26 (15 mg, 9.8 μmol) was dissolved in N,N-dimethylformamide (1.2 mL) under Argon. Compound 48 (23.8 mg, 39 μmol) and cesium carbonate (31.9 mg, 98 μmol) was added. The mixture was sonicated for 10 min and then stirred for 1 hr 50 min. The reaction was monitored by HPLC (gradient from 0 to 30% acetonitrile in 0.1% aqueous trifluoroacetic acid, 30 min). The mixture was diluted with 0.1% aqueous trifluoroacetic acid (24 mL) and lyophilized. Preparative HPLC (gradient from 13 to 18% acetonitrile in 0.1% aqueous trifluoroacetic acid, 30 min) gave 49 (17.8 mg, 88%).

Retention times (analytical runs): 48: 10.1 min, 49: 21.9 min, 26: 24.4 min.

Conjugate 50

Peptide 32 (15 mg, 21.1 μmol) was dissolved in a mixture of dimethylsulfoxide (0.6 mL) and N,N-dimethylformamide (0.6 mL) under Argon. The mixture was sonicated for 1 min. Compound 48 (29.6 mg, 48 μmol) and cesium carbonate (39.4 mg. 121 μmol) was added. The mixture was sonicated for 15 min and then stirred for 1 h 50 min. The reaction was monitored by HPLC (gradient from 0 to 30% acetonitrile in 0.1% aqueous trifluoroacetic acid, 30 min). The mixture was diluted with 0.1% aqueous trifluoroacetic acid (24 mL) and lyophilized. The crude product was pooled with an additional batch prepared analogously from 5 mg of peptide. Preparative HPLC of the pooled material (gradient from 7 to 12% acetonitrile in 0.1% aqueous trifluoroacetic acid, 30 min) gave 50 (14.3 mg, 74%).

Retention times (analytical runs): 48: 10.1 min, 50: 15.2 min, 26:16.8 min.

Conjugate 51

Peptide 19 (15 mg, 10 μmol) was dissolved in N,N-dimethylformamide (0.4 mL) under Argon. Compound 55 (6 mg, 8.3 μmol) and cesium carbonate (56 mg, 172 μmol) was added. The mixture was sonicated for 10 min and then stirred for 2 h. The reaction was monitored by HPLC (gradient from 0 to 30% acetonitrile in 0.1% aqueous trifluoroacetic acid, 30 min). The mixture was diluted with 0.1% aqueous trifluoroacetic acid and lyophilized. Preparative HPLC (gradient from 10 to 14% acetonitrile in 0.1% aqueous trifluoroacetic acid, 30 min) gave 51 (8.2 mg, 45%).

Retention times (analytical runs): 55: 13.0 min. 52: 20.3 min, 19: 21.3 min.

Conjugate 52

Peptide 20 (5 mg, 3 μmol) was dissolved in N,N-dimethylformamide (0.4 mL) under Argon. Compound 55 (4.3 mg, 6 μmol) and cesium carbonate (37 mg, 114 μmol) was added. The mixture was sonicated for 5 min and then stirred for 3 h 45 min. The reaction was monitored by HPLC (gradient from 0 to 30% acetonitrile in 0.1% aqueous trifluoroacetic acid, 30 min). The mixture was diluted with 0.1% aqueous trifluoroacetic acid (8 mL) and lyophilized. The crude product was pooled with an additional batch prepared analogously from 5 mg of peptide. Preparative HPLC of the pooled material (gradient from 13 to 18% acetonitrile in 0.1% aqueous trifluoroacetic acid, 30 min) gave 52 (9.3 mg, 65%).

Retention times (analytical runs): 55: 13.0 min, 52: 22.7 min, 20: 23.6 min.

TABLE 2

| Starting material (Nos.) | Method | Reaction conditions | Isolated product (No.) | Yield (%) | Analysis |
|---|---|---|---|---|---|
| 9 + 16 | A | DMSO, 1000 μL[a], 1.5 h | 21 | 11 | HPLC[c] |
| 9 + 17 | A | DMSO, 750 μL[a], 2.5 h | 22 | 10 | HPLC[c] |
| 9 + 18 | A | DMSO, 500 μL[a], 2.5 h | 23 | 29 | HPLC[c], [M + H] + 1943[d] |
| 15 + 19 | B | DMF, 400 μL[b], 5 h | 24 | 59 | HPLC[c], [M + H] + 1788[d] |
| 15 + 20 | B | DMF, 400 μL[b], 1 h | 25 | 60 | HPLC[c], [M + H] + 1761[d] |
| 28 + 20 | B | DMF, 1300 μL[b], 3 h | 29 | 70 | HPLC[c], [M + H] + 1469[d] |
| 28 + 26 | B | DMF, 615 μL[b], 2 h | 30 | 90 | HPLC[c], [M + H] + 1564[d] |
| 28 + 19 | B | DMF, 600 μL[b], 3 h | 31 | 75 | HPLC[c], [M + H] + 1497[d] |
| 28 + 38 | B | DMF, 525 μL[b], 1.5 h | 40 | 52 | HPLC[c], [M + H] + 1342[d] |
| 28 + 39 | B | DMF, 500 μL[b], 1.3 h | 41 | 86 | HPLC[c], [M + H] + 1320[d] |

TABLE 2-continued

| Starting material (Nos.) | Method | Reaction conditions | Isolated product (No.) | Yield (%) | Analysis |
|---|---|---|---|---|---|
| 28 + 36 | B | DMF, 560 μL[b], 2.1 h | 42 | 95 | HPLC[c], [M + H] + 1426[d] |
| 28 + 37 | B | DMF, 545 μL[b], 1.75 h | 43 | 73 | HPLC[c], [M + H] + 1273[d] |
| 28 + 32 | B | DMSO, 500 μL[b], 1.2 h | 44 | 54 | HPLC[c], [M + H] + 1380[d] |
| 28 + 34 | B | DMF, 590 μL[b], 2.2 h | 45 | 63 | HPLC[c], [M + H] + 1382[d] |
| 28 + 35 | B | DMF, 600 μL[b], 4.3 h | 46 | 56 | HPLC[c], [M + H] + 1396[d] |
| 28 + 33 | B | DMSO, 500 μL[b], 2.1 h | 47 | 59 | HPLC[c], [M + H] + 1382[d] |
| 48 + 26 | B | DMF, 612 μL[b], 2 h | 49 | 88 | HPLC[c], [M + H] + 1726[d] |
| 48 + 32 | B | DMSO + DMF (1:1), 495 μL[b], 2.1 h | 50 | 74 | HPLC[c], [M + H] + 1542[d] |
| 55 + 19 | B | DMF, 200 μL[b], 2.2 h | 51 | 45 | HPLC[c], [M + H] + 1769[d] |
| 55 + 20 | B | DMF, 665 μL[b], 3.8 h | 52 | 65 | HPLC[c], [M + H] + 1741[d] |

[a]μL/10 mmol peptide.
[b]μL/5 μmol peptide.
[c]The product was in all cases faster moving than the peptide starting material and slower moving than the carbohydrate starting material.
[d]FAB-MS data were in agreement with the theoretical values.

2. IN VIVO PRIMARY INDUCTION OF VIRUS-SPECIFIC CTL BY IMMUNIZATION WITH 9-MER SYNTHETIC PEPTIDES 2.1. Methods In vivo primary induction of cytotoxic T lymphocytes (CTL) by immunization with the novel conjugates of the present invention can be carried out by methodology analogous to what is described below for in vivo primary induction of virus-specific CTL by immunization with 9-mer synthetic peptides.

Vaccination of mice with pre-processed synthetic peptides, corresponding to endogenous 9-mers produced in influenza A virus-infected cells resulted in strong primary CTL responses. The generated CTL efficiently killed virus-infected target cells with preference for viral strains having the identical amino acid sequences to the peptides used for immunization. The optimal conditions for a primary in vivo CTL response was obtained with 100 μg peptide dissolved in IFA and injected s.c. at the base of tail. Spleen cells which had been primed 7–10 days earlier were restimulated for 5 days in vitro, using an optimal low peptide concentration (0.05 μM) and tested against virus-infected and peptide-treated target cells. The peptide-induced CTL were MHC class I restriced and CD8 positive.

Peptides

The peptide ASNENMETM (designated as pep 9(PR8); SEQ ID NO: 1) and ASNENMDAM (designated as pep 9(NT60); Residue 3–11 of SEQ ID NO: 4) are from the NP366–374 of influenza A virus strains A/PRI8/34 and A/NT/60/68, respectively. Pep 9(PR8) was synthesized using an Applied Biosystems 430A peptide synthesizer (Applied Biosystems, Inc., Foster City, Calif.). Pep 9(NT60) was synthesized by the solid phase "tea bag" (Houghten, 1985; Sällberg, 1991). All peptides were purified by reverse-phase HPLC and analysed for amino acid composition by plasma desorption mass spectrometry. Stock solutions of peptides were prepared in PBS and stored at −20° C.

Immunization

Mice were immunized by one s.c. injection of 100 μg each free synthetic peptides dissolved in IFA at the base of the tail or by one intravenous injection of 20 HAU of influenza A virus diluted in PBS and used between 1–2 week after the immunization.

In vitro generation of influenza A virus-specific CTL

Immune spleen cells were prepared into cell suspension. The red cells were lysed using lysis buffer consisting of $NH_4Cl$ 8.29 g, $KHCO_3$ 1.0 g, EDTA 0.0372 g per 1 liter distilled water (pH 7.4). $25\times10^6$ responder spleen cells from in vivo primed mice were cocultured with $25\times10^6$ irradiated (2000 rad) syngeneic spleen cells, either infected by influenza A virus or in the presence of 0.05, 0.5 and 5 μM peptides in 50-ml tissue culture flask (Costar, Cambridge, Mass.) with 10 ml complete medium for 5 days at 37° C. in humidified air with 5.3% $CO_2$.

Cytotoxicity assay

As previously described (Jondal, 1975), virus-infected or peptide-coated target cells were prepared by infecting $2\times10^6$ cells with 320 HAU virus for 1.5 h or incubated with 50 μM peptides for 1.5 h at 37° C., respectively. After washing, the cells were labelled with 100–200 μCi of $Na_2{}^{51}CrO_4$ for 1 h. The cells were washed twice, and $10^4$ target cells in 50 μl were added to 100 μl of varying numbers of effector cells which had been washed three times prior to the assay in 150 μl of complete medium in 96-well V-bottomed plates and were incubated for 4 h at 37° C., 5.3% $CO_2$. After incubation, the 50 μl supernatant was collected and the percentage of specific $^{51}Cr$ release was calculated by the formula: % specific release=(experimental-spontanous)/(maximal-spontanous) cpm.

Spontanous release was always less than 15%.

2.2. Results

Primary in vivo induction of anti-influenza A virus-specific CTL with 9-mers. mers.

As previously reported (Townsend et al., 1985, 1986), CTL induced with live influenza A virus in H-$2^b$ mice are mainly directed against the immunodominant NP365–380 epitope. We initially tried to immunize mice with peptide NP365–380 derived from both PR8 and NT60 strains to induce CTL responses according to a protocol described by Alchele et al. (1990). However, an insignificant level of killing activity against both peptide-coated and virus-infected cells was observed in spite of repeated boosting. Instead, when 100 μg of the shorter pep 9(PR8) was used for s.c. injection and spleen cells restimulated with 5 μM pep 9(PR8) in vitro, a strong CTL response against pep 9(PR8)-coated RMA (not shown) and EL4 cells was elicited although virus-infected target cells were not killed (Table 3). When a lower concentration of pep 9(PR8) was used for restimulation in vitro, the generated CTL had a higher killing activity against pep 9(PR8)-coated target cells and virus-infected cells were also lysed (Table 3). As shown in Table 3, the optimal dose for immunization was 100 μg and for restimulation 5 or 0.05 μM. Immunization with 10 μg and 1 μg generated less or even no CTL response. Peptide dissolved in complete Freunds adjuvant (CFA) or PBS gave no response. Intravenous injection of peptides did not generate a primary in vivo CTL response either (not shown).

Another 9-mer derived from NT 60 gave stronger anti-peptide and antiviral CTL responses, as shown in FIG. 3.

Specificity of CTL induced by pep 9(PR8) and pep 9(NT60)

In the light of these results we investigated the fine specificity of the generated CTL in relation to pep 9(PR8) and pep (NT60). CTL preferentially killed their corresponding peptide-coated and virus-infected cells (FIG. 4). CTL showed a higher cross-reactivity with peptide-coated cells than with virus-infected target cells.

CTL responses to live virus or peptides

Mice were primed with live PR8 virus and immune spleen cells were restimulated with either virus-infected stimulator cells (FIG. 5A) or normal syngeneic spleen cells in the presence of 0.05 μM pep 9(PR8) (FIG. 5B). CTL primed in vivo with live virus and restimulated with low concentration of pep 9(PR8) had a remarkable ability to recognize both virus-infected and peptide-coated cells (FIG. 5B). It should be noted that the low amount of restimulation peptide was sufficient to stimulate virus-primed CTL in vitro and had the same potency as virus-infected cells did. When pep 9(PR8) was used for in vivo priming and virus-infected cells or pep 9(PR8) for restimulation in vitro (FIG. 5C and D), CTL responses were generated against both peptide-coated and virus-infected cells. Live virus had a higher efficiency to prime CTL than the free peptide.

Time course of CTL activity after immunization with pep 9(PR8)

In order to determine the kinetics of CTL activity after immunization with pep 9(PR8), mice were primed once with pep 9(PR8). Spleen cells of immunized animals were restimulated in vitro 2–30 days after immunization with pep 9(PR8) and assayed for CTL activity. The CTL activity against pep 9(PR8)-coated RMA target cells reached a peak 7 days after the immunization and the activity gradually declined afterwards (FIG. 6). At the day 30 after priming, a lower level of CTL activity could still be detected.

In vivo Peptide-induced cytotoxicity is mediated by $CD8^+$ and MHC class I-restricted As shown in FIG. 7a, pep 9(PR8)-induced CTL depleted for $CD8^+$ T cells failed to lyse pep 9(PR8)-coated EL4 cells. On the other hand, depletion of $CD4^+$ T cells did not affect the cytolytic activity against pep 9(PR8)-coated target cells. Thus, pep 9(PR8)-specific CTL express the $CD4^-$ $CD8^+$ phenotype.

In vivo peptide-primed CTL of C57B6/J (H-$2^b$) origin were tested on syngeneic EL4 (H-$2^b$), allogeneic P815 (H-$2^d$) and L929 (H-$2^k$) target cells infected with influenza PR8 strain. As FIG. 7b shows, there is a clear restriction specificity for H-$2^b$ target cells.

TABLE 3

CTL activity induced by different doses of peptides for priming in vivo and restimulation in vitro.

| Priming dose (μg) | Restimulation dose (μM) | Untreated | | PR8-infected | | pep9(PR8)-coated | |
|---|---|---|---|---|---|---|---|
| | | 40:1* | 20:1 | 40:1 | 20:1 | 40:1 | 20:1 |
| 100 | 5.00 | 4.61 | 4.21 | 7.00 | 8.50 | 43.68 | 34.73 |
| | 0.05 | 0.12 | 0.51 | 30.76 | 30.07 | 59.42 | 50.73 |
| 10 | 5.00 | 5.63 | 4.19 | 15.04 | 13.98 | 23.54 | 22.09 |
| | 0.05 | 5.74 | 4.14 | 31.19 | 23.75 | 45.52 | 34.60 |
| 1 | 5.00 | 3.34 | 2.66 | 6.88 | 5.54 | 11.85 | 9.28 |
| | 0.05 | 4.08 | 3.32 | 12.43 | 10.50 | 16.44 | 15.54 |

*Effector:target ratio.

3. EXTERNAL MHC-1 BINDING PEPTIDES ARE RECYCLED TO THE CELL SURFACE AFTER INTERNALIZATION

External peptides that bind MHC-1 are known to upregulate the expression of the corresponding restriction element in the presence of $B_2$-M (Otten et al., 1992). This upregulation response in vitro correlates with the in vivo immunogenicity of peptides. As we have found that the endosomal inhibitor chloroquine inhibits this upregulation (FIG. 8), it is possible that this process require peptide internalization and membrane recycling. In support of this model a number of earlier studies have found internalization of MHC-1 through chlatrin coated pits, and also MHC-1 recycling.

To study the possible recycling of external MHC-1 binding peptides we synthesized two $D^b$ binding peptides that represented immunodominant epitopes on the E1A protein from adenovirus (sequence SGPSNTPPEI; SEQ ID NO: 2) and on the nucleoprotein from influenza A virus (PR8) (sequence ASNENMETM; SEQ ID NO: 1). Cystein was added to the amino-or carboxytermini, as a biochemical coupling site for the molecular marker galabios (Gal-Gal), for which a specific monoclonal antibody was available (MC2101) (Brodin et al. 1988). As earlier reported, the addition of cystein to the aminoterminus did not abrogate the $D^b$ upregulating capacity, or the in vivo immunogenicity of the peptide (Zhou et al., 1992 b). The addition of galabios at the same site, generated glycopeptides which were strongly recognized by the galabios specific monoclonal antibody MC2101 in an ELISA test (Table 4). The $Gal_2$-CSG11 peptide (conjugate 29) reacted stronger than the $GAL_2$-CAS10 peptide. To verify that the additional galabios did not alter the $D^b$ binding capacity or the in vivo immunogenicity, both glycopeptides were tested for in vitro $D^b$ upregulation and for in vivo immunogenicity. $D^b$ upregulation was similar with glycopeptides, as compared to peptides alone (data not shown). CTL:s generated by in vivo injection, and in vitro restimulation with glycopeptides were strictly peptide specific and did not recognize $Gal_2$ when presented by another peptide, in a criss-cross fashion (FIG. 9). From these results we conclude that $Gal_2$, in the glycopeptides, acted as an inert marker.

To allow maximum binding of external glycopeptides to membrane $D^b$ molecules, mutant RMA-S cells were used. These cells are inherently deficient in transporting processed peptides from the cytosol to the ER compartment by the loss of the Tap-2 peptide transporter system. As a consequence, RMA-S cells express a higher fraction of empty $D^b$ molecules, than non-mutant cells, at the cell surface. The expression of these empty $D^b$ molecules can be further increased by low temperature (26° C.), and stabilized by the addition of $D^b$ binding peptides at 37° C. (FIG. 3). Thus, by treating low temperature induced RMA-S cells with a high concentration of glycopeptides, in the presence of $B_2$-M, a large fraction of membrane $D^b$ molecules became saturated with the same, identical glycopeptide. RMA-S cells treated this way are clearly stained with the MC2101 antibody (FIG. 10), demonstrating membrane expression of the $Gal_2$ epitope, presumably in the form of MHC-1 bound glycopeptide. By pronase treatment, all $D^b$ and $Gal_2$ expression is removed from these cells (FIG. 10). If these cells are then transferred to 37° C. and incubated for 1 hour, both $D^b$ and $Gal_2$ expression return to the cell surface (FIG. 10). The return of the $Gal_2$ epitope was inhibited by chloroquine (data not shown). As the conventional MHC-1 presentation pathway is non-functional in RMA-S cells, and consequently cytosolic peptides are not transported into the ER compartment, the results strongly indicate endosomal recycling of the $D^b$ binding glycopeptides. Similar results were obtained with the $Gal_2$-CAS10 glycopeptide (not shown).

To verify these results, on a functional level, influenza A (PR8) specific CTL were generated, and tested against RMA-S and EL-4 target cells treated with a peptide (ASNENMETM) corresponding to the target epitope in the $Gal_2$-CAS10 glycopeptide (conjugate 31). Both target cells were strongly killed, as earlier reported (Rötzshke et al., 1990) (FIG. 11). Pronase treatment of these peptide treated target cells, removed most $D^b$ expression, and most of the sensitivity to the specific CTL:s (FIG. 11). Incubation of pronase treated cells at 37° C., to allow re-expression of both $D^b$ and associated peptides, resulted in a return of susceptibility to CTL killing. This return was faster and more extensive with RMA-S cells as compared to EL-4 cells, and was blocked by anti-$D^b$ monoclonal antibodies and by chloroquine (data not shown).

We interpret the present results to mean that MHC-1 bound peptides recycle through an intra-cellular compartment similar to early endosomes in T cells. Possibly this mechanism may allow for peptide exchange to occur in order to optimize the expression of membrane peptides. Hochman et al. (1991) have shown that class I MHC molecules undergo conformational changes in an endosomal compartment, indicating that $B_2$-M is going off and on the heavy chain. Thus, the low pH that cause this effect, may also allow for peptide exchange to occur. In support of this notion, Harding (1992) has recently reported that MHC-1 presentation can be blocked by hypothermia and weak base amines, using electroporation of exogenous antigen.

MHC-1 molecules are known to bind optimal length peptides with a much higher affinity, as compared to slightly longer peptides, a phenomenon that is reflected in a number of in vitro assays. These include MHC-1 membrane upregulation, target cell sensitization to specific CTL, direct binding of peptide to empty class I chains on mutant cells, peptide-induced MHC-1 assembly in lysates from mutant cells and measurements of off rates of bound peptides from MHC-1. This higher affinity of optimal length peptides may be related to an exact fit into the peptide binding groove of class I chains, as this groove is closed at both ends (Madden et al., 1991). Thus, the optimally sized peptide may form a trimeric peptide-heavy chain $B^2$-M complex, which is more likely to recycle from endosomes, as compared to complexes consisting of longer peptides.

In target T cells, recycling of optimal MHC-1 bound peptides, may allow for the most efficient recognition by the corresponding, specific CTL:s, as in the present work. So far, most evidence for MHC-1 recycling has been obtained in T cells. However, if similar mechanisms operate in certain antigen presenting cells, the build-up of optimal peptides, at the membrane level, may also be important in the afferent arm of the immune response. In particular, dendritic cells, known to be crucial for CTL generation, both in vivo and in vitro, should be investigated in this aspect. The existing correlation between the capacity of peptides to upregulate MHC-1 expression in vitro, and their in vivo immunogenicity, suggests that this maybe an important mechanism in the cellular response.

TABLE 4

Recognition of $Gal_2$ glycopeptides by monoclonal antibody MC2101 in ELISA assay.

| | | Absorbance at 405 nm | | | |
|---|---|---|---|---|---|
| Antibody | Specificity | $Gal_2$-CSG11 | CSG-11 | $Gal_2$-CAS10 | CAS-10 |
| MC2101 | Galabios Gal-Gal | 1.86 | 0.01 | 0.41 | 0.02 |
| Pk002 | Globotriaosyl Gal-Gal-Glc (CD77) | 0.04 | 0.08 | 0.04 | 0.01 |

Peptides (50 μg/ml) were diluted in 0.05M carbonate buffer (pH 9.6) and 100 μl/well was added to flat-bottomed Costar microplates (cat. No 3590) for incubation over-night at 4° C. Plates were washed once with PBS, pre-incubated with 0.5% PBS for 30 minutes at room temperature and washed twice with PBS/0.05% Tween buffer. Monoclonal antibodies were diluted in 0.5% gelatin/PBS/0.05% Tween, added to microplates and incubated for 2 hours at room temperature, and flick-washed with PBS/Tween. Alkaline phosphatase conjugated rabbit anti-mouse immunoglobulins (Dakopafts code No. S 414) was diluted 1/1000 in PBS/Tween and added as 100 μl/well. After 2 hours incubation at room temperature and 4 washes with PBS/Tween, 100 μl of alkaline phosphatase substrate solution was added. Plates were read after 2 hour at room temperaure, using a Multi-skan System (Lab systems), for optical density at 405 nm.

4. GENERATION OF A CARBOHYDRATE SPECIFIC CTL RESPONSE BY VACCINATION WITH A GLYCO-PEPTIDE WHICH HAS THE CARBOHYDRATE PART IN AN INTERNAL, IMMUNOGENIC POSITION.

The carbohydrate galabiose (Gal-α-4Gal otherwise referred to as $Gal_2$) was coupled to an internal cystein (position 10) in the 12-mer peptide SGVENPGGYCLT (SEQ ID NO: 9) which represents an $H2-D^b$ restricted immunodominant CTL epitope in the lymphocytic chori-omeningitis virus (LCMV) (Oldstone et al., 1988). The glycopeptide was called $SGV12-Gal_2$ (conjugate 30; FIG. 12). The coupling was done to a thiol group, using S bonding, as described i Example 1.

Mice were immunized with the $SGV12-Gal_2$ glycopeptide, as described in Example 2 and in Zhou et al.(1992 a). After restimulation in vitro with the same $SGV12-Gal_2$ glycopeptide, the generated cytotoxic T cells were tested against $H2-D^b$ and $K^b$ positive EL-4 cells, coated with the following peptides and glycopeptides:

1. SGVENPGGYCLT (SGV12; SEQ ID NO: 9)
2. $SGV12-Gal_2$
3. ASNE NSETM (ASN9; SEQ ID NO: 1) with $Gal_2$ bound to S in position 6. ($ASN9-6S-Gal_2$)
4. ASN9-6S
5. $CSG11-Gal_2$ (see Example 3 and FIG. 9)
6. CSGPSNTPPEI (CSG11; SEQ ID NO: 8)
7. CRG9 with $Gal_2$ bound to C in position 1 ($CRG9-Gal_2$)
8. CRGYVYQGL (CRG9; SEQ ID NO: 13)

Peptides 1–6 are known, modified $D^b$ binding T cell epitopes, and bind to RMA-S cells, as measured by $D^b$ upregulation in vitro (data not shown). Peptides 7–8 represent a known $K^b$ epitope (RGYVYQGL; SEQ ID NO: 27), and both peptides upregulate $K^b$ on RMA-S cells (data not shown). The expression of the $Gal_2$ epitope was measured by FACS on the surface of cells that have bound glycopeptides. A high $Gal_2$ expression was found with glycopeptides 2, 5 and 7 (data not shown). Glycopeptide 3 was not recognized by anti-$Gal_2$ monoclonal antibodies when bound to RMA-S cells. The conclusion was that glycopeptides 5 and 7 expressed the same $Gal_2$ epitope as the immunogen $SGV12-Gal_2$ on different carrier peptides. The $CSG11-Gal_2$ glycopeptide was bound to $D^b$ and the CRG9-Gal, glycopeptide to $K^b$. Thus, the only epitope that is shared between glycopeptides 2, 5 and 7 is $Gal_2$.

When the $SGV12-Gal_2$ generated CTL cells were tested against EL-4 cells coated with the above described peptides and glycopeptides, it was found that target cells coated with glycopeptides 2 and 5 were killed, and also, at a lower level, target cells coated with glycopeptide 7 (FIG. 13). Thus, the generated CTL cells did not recognize the carrier peptide alone (SGV12), or the other control peptides, including glycopeptide 3 (which does not express the $Gal_2$ epitope at the cell surface level).

From the above results, it is concluded that immunization with the glycopeptide $SGV12-Gal_2$, generates a $Gal_2$ specific T cell response. The reason for this may be that the $Gal_2$ carbohydrate part is oriented in an optimal position for T cell recognition. The higher killing of glycopeptide 5 coated target cells, as compared to glycopeptide 7 coated target cells, may be due to the fact that glycopeptide 5 is presented by $D^b$ and glycopeptide 7 by $K^b$ class I chains.

In a further set of experiments (adopting the same protocol as described above) mice were immunised with glycopeptide $RGY8-4h-Gal_2$ ("RGY8" represents the octapeptide RGYVYQGL; 4 h indicates that the V in position 4 is replaced by homoserine; $Gal_2$ indicates conjugation of the sugar $Gal_2$ to the homoserine hydroxyl). As in the experiments described with reference to FIG. 13, the resulting RGY8-4 h-$Gal_2$ generated CTL cells were tested against EL-4 cells coated with $RGY8-4h-Gal_2$ and RGY8–4 h.

From the results shown in FIG. 14(A) it can be seen that both peptide and glycopeptide specific CTL cells are generated.

When this heterogeneous effector cell population was tested against EL-4 cells coated with $Gal_2$ on another carrier peptide ($SGV12-Gal_2$) and the SGV12 peptide per se (FIG. 14(B)), only the cells coated with glycopeptide were killed.

This effect proves that the CTLs have $Gal_2$ specificity by "crisscross" testing (see the section headed "Experimental Test System" above).

The data presented herein may be summarised in the following Tables 5 and 6.

TABLE 5

Analysis of $K^b$ binding peptides and glycopeptides

| Peptide | ELISA | MHC-1 upreg | Membrane express | Immuno-genic | Specificity P | G | GP |
|---|---|---|---|---|---|---|---|
| $Gal_2$-CAP9 | + | + | − | + | + | | |
| FAP9-5h-$Gal_2$ | + | | | + | + | + | |
| $Gal_2$ -CRG9 | + | − | + | + | + | | |
| RGY8-4h-$Gal_2$ | + | + | + | + | + | + | |

| Peptide | | Immunogenic | Comments |
|---|---|---|---|
| CAP9 | (SEQ ID NO: 14) | + | |
| FAP9 | (SEQ ID NO: 20) | + | Strong, with high FAP9-5h reactivity |
| FAP9-5h | (SEQ ID NO: 26) | + | Weaker, low FAP9 reactivity |
| CRG9 | (SEQ ID NO: 13) | + | |
| RGY8 | (SEQ ID NO: 27) | + | Some RGY8-4h reactivity |
| RGY8-4h | (SEQ ID NO: 25) | + | Strong, with RGY8 reactivity |

TABLE 6

Analysis of $D^b$ binding peptides and glycopeptides

| Peptide | ELISA 7.4 | ELISA 9.6 | MHC-1 upreg | Membrane express | Membrane recycle | Immuno-genic | Specificity P | Specificity G | Specificity GP |
|---|---|---|---|---|---|---|---|---|---|
| Gal$_2$-CAS10 | | + | + | + | + | + | + | | |
| GM3-CAS10 | | | | | | − | | | |
| GM3-laktam-CAS10 | | | | | | tox | | | |
| ASN9-6h-Gal$_2$ | + | − | + | + | + | + | + | | |
| ASN9-6S-Gal$_2$ | | − | + | − | | − | | | |
| ASN9-4S-Gal$_2$ | (+) | − | | − | | | | | |
| Gal$_2$-CSG11 | | + | + | + | + | + | + | | |
| GM3-CSG11 | | | | | | − | | | |
| GM3-laktam-CSG11 | | | | | | + | + | | |
| SGP10-6h-Gal$_2$ | + | + | + | + | + | − | | | |
| SGP10-6S-Gal$_2$ | | − | + | − | | − | | | |
| SGP10-4S-Gal$_2$ | (+) | − | | − | | | | | |
| SGV12-Gal$_2$ | | + | + | + | + | + | | + | |

| Peptide | | Immunogenic |
|---|---|---|
| CAS10 | (SEQ ID NO: 7) | + |
| ASN9 | (SEQ ID NO: 1) | + |
| ASN9-6h | (SEQ ID NO: 21) | |
| ASN9-6S | | − |
| ASN9-4S | | |
| CSG11 | (SEQ ID NO: 8) | + |
| SGP10 | (SEQ ID NO: 2) | + |
| SGP10-6h | (SEQ ID NO: 23) | |
| SGP10-6S | | + |
| SGP10-4S | | |

Note on Assays (Tables 5 and 6):
ELISA
The ELISA assay was performed as described in connection with Table 4.
MHC-1 upregulation
As described above in relation to FIG. 8 and FIG. 10A, the principle is that peptides can bind to empty MHC-1 heavy chains at the cell surface on antigen-presenting cells, and this leads to a stabilization, and upregulation of the corresponding MHC-1 chain.
Membrane expression
When the glycopeptide bind to MHC-1, on the cell surface, the expression (and acessibility) of the corresponding CHO part, can be detected by antibody staining in FACS, as described above in relation to FIG. 10C and E.
Membrane recycling
Described in FIG. 10D and F.
Immunogenicity
Mice are immunized with glycopeptides and described herein, and in vitro restimulated CTL cells are tested for killing of target cells coated with different peptides and glycopeptides. Specificity P means that the CTL cells only recognize the peptide part G only the CHO part and GP only the combination.

BRIEF DESCRIPTION OF DRAWINGS

FIG. 1 Chemical structure of compounds 1–15, described under the section "Synthesis of spacer arm glycosides"

FIG. 2 Chemical structure of glycopeptide products 21–25, described under the section "Synthesis of glycopeptides".

FIG. 3 CTL induced by pep9(NT60) more efficiently lysed both virus specific and peptide-coated EL4 cells with 0.05 μM pep 9(NT60) used for restimulation than with 5 μM and 0.5 μM. CTL were generated by one s.c. injection of 100 μg pep 9(NT60). Immune spleen cells were restimulated with syngeneic irradiated spleen cells in the presence of pep 9(NT60) (A), 5 μM; (B), 0.5 μM and (C), 0.05 μM for 5 days and tested against EL4 untreated (○—602), NT60-infected (●—●), pep 9(NT60)-coated (□—□).

FIG. 4 Specificity of CTL induced by pep 9(PR8) (A) and pep 9(NT60) (B). The effector CTL were tested against EL4 untreated (○—○), PR8-infected (●—●), NT-60 infected (□—□), pep 9(PR8)-coated (■—■), pep 9(NT60)-coated (△—△).

FIG. 5 CTL responses primed and restimulated with live virus and peptides. Mice were primed in vivo with PR8 live virus (A, B) or pep 9(PR8) (C, D), and restimulated with PR8-infected spleen cells (A, C) or irradiated spleen cells in the presence of 0.05 μM pep 9(PR8) (B, D). Target cells were EL4 untreated (○—○), PR8-infected (●—●), pep 9(PR8)-coated (□—□).

CTL assay. (B and D). Mice were immunized s.c. at the base of tail with 100 μg glycopeptide in incomplete Freunds Adjuvant. Ten days after priming, spleen cells were re-stimulated in vitro using $25 \times 10^6$ responder cells co-cultured with $25 \times 10^6$ irradiated (2500 rad) syngeneic spleen cells. Re-stimulation was done in the presence of glycopeptides at 0.05 μM in 50 ml tissue culture flasks with RPMI/10% FCS at 37° C. for five days. RMA-S target cells were coated with 50 μM peptide for 1 hour at 37° C. and washed. Cells were labelled with 100 μCi $Na_2{}^{Cro}{}_4$ for one hour at 37° C. and washed twice. Effector lymphocytes were separated by Lymphoprep centrifugation and tested at different ratios with 5000 $^{51}$Cr-labelled target cells, using 150 μl/well in V-shaped microtiter wells. Microplates were centrifuged at 300 g and incubated for 4 hours at 37° C. After incubation plates were centrifuged again and 50 μl supernatants were assayed in a gamma scintillation counter.

FIG. 10 Panel A: RMA-s cells were incubated for 24 hours at 26° C. to induce expression of empty $D^b$ MHC-1 chains at the cell surface, and at 37° C., and stained for $D^b$ expression. Panel B: Removal of $D^b$ expression by pronase treatment of RMA-S cells, preincubated at 26° C. Pronase treatment for 2 h and 4 h. $D^b$ removal is complete at 4 h. Panels C and E: 26° C. induced RMA-S cells were treated with the glycopeptides $Gal_2$-CSG11 (panel C) or $Gal_2$CAS10 (panel E), 300 μM for 2 h at 37° C., washed and stained for $Gal_2$ expression. Panels D and F. Glycopeptide treated RMA-S cells as in panels C and E were pronase treated to remove $D^b$ and glycopeptide expression, washed and further incubated at 37° C. to allow re-expression of glycopeptides and stained for $Gal_2$ expression.

Figure 6:
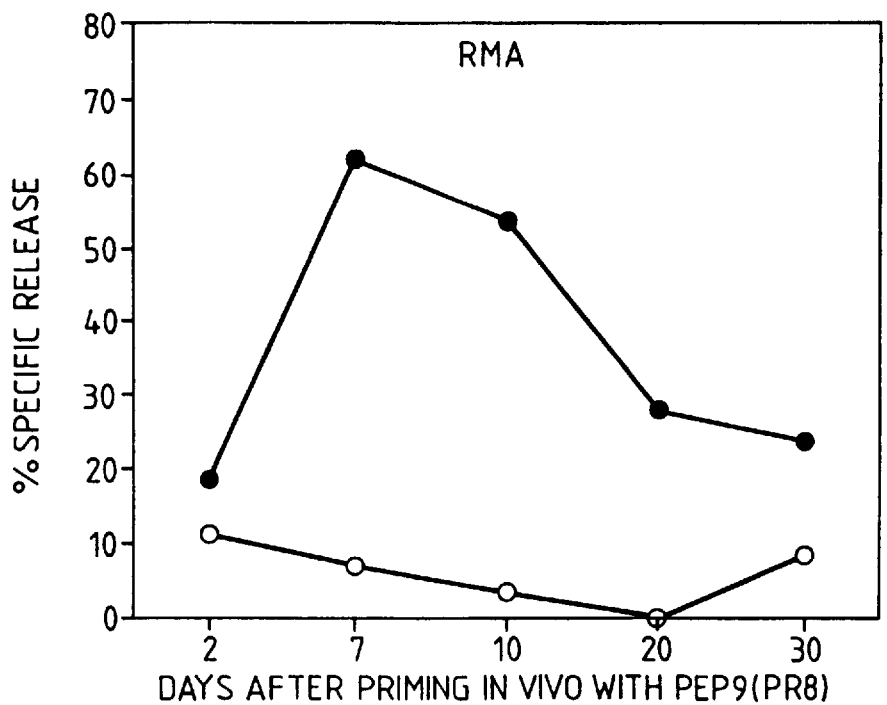
FIG. 6 Kinetics of CTL activity induced by one s.c. injection of pep 9(PRB). Mice were primed with 100 μg pep 9(PR8) in vivo and restimulated in vitro with 5 μM pep 9(PR8) at day 2, 7, 10, 20 and 30 after priming. The generated CTL were tested against RMA untreated (○—○) and pep 9(PR8)-coated (●—●). Effector:target ratio, 60:1.
Figure 8:
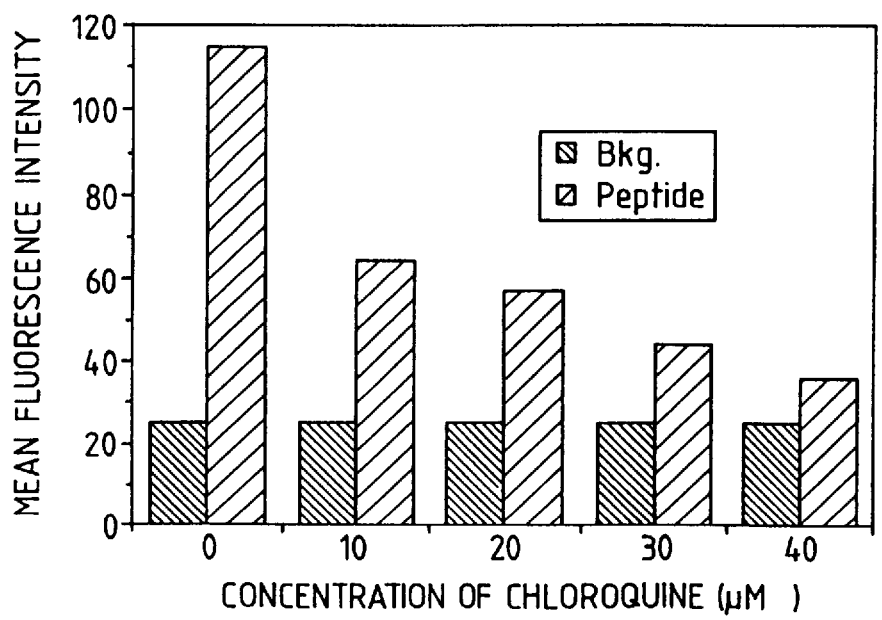
FIG. 8 Peptide mediated H-2D$^b$ up-regulation can be inhibited by chloroquine. RMA-S cells were incubated with influenza A (PR8) peptide NP366–374 (50 μM) in the presence or absence of chloroquine for 6 h. After incubation, cells were washed, stained with anti-$D^b$ (28-14-8S) monoclonal antibody on ice for 30 minutes, washed and incubated with rabbit anti-mouse (F(ab')2-FITC (F313, Dako, Copenhagen, Denmark) for 30 minutes. The stained cells were fixed with 1% formaldehyde and analysed in a FAC-Scan flow cytometer (Becton Dickinson; Mountain View, Calif.).
Figure 7A:
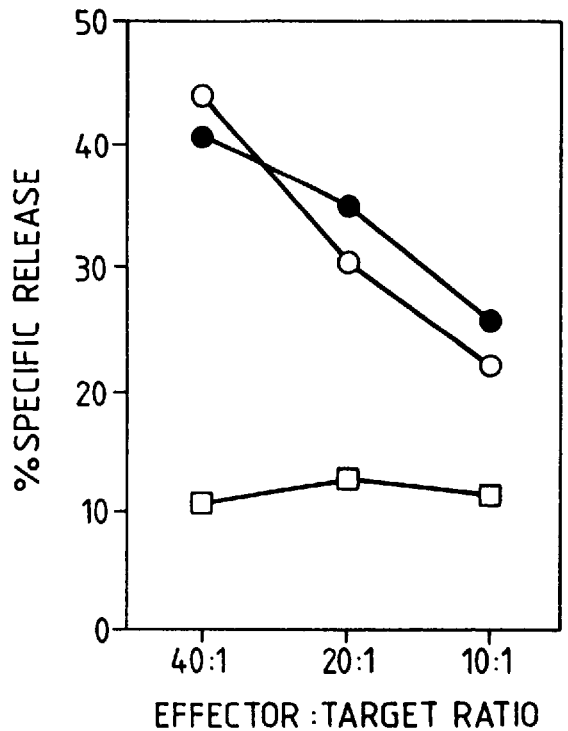
FIG. 7 Peptide-induced cytotoxicity is mediated by CD8$^+$ and H-2D$^b$ restricted T cells. a: CTL were induced by pep 9(PR8). Equal numbers of CTL were then depleted for CD4$^+$ and CD8$^+$ T cells using the Dynabeads system. The remaining cells were then tested for lytic activity against pep 9(PR8)-coated EL4 cells. Untreated CTL (○—○), CD4$^+$ depleted (●—●) and CD8$^+$ depleted (□—□) were tested for lytic activity against pep 9(PR8)-coated EL4 cells. b: CTL induced by pep 9(PR8) were tested against PR8-infected EL4 (○—○), PR8-infected P815 (●—●) and PR8-infected L929 (□—□)
Figure 7B:
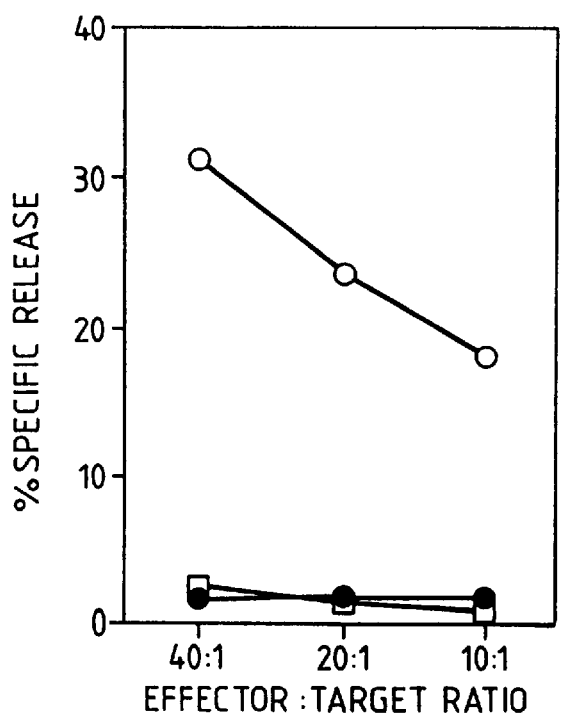
Figure 9A:
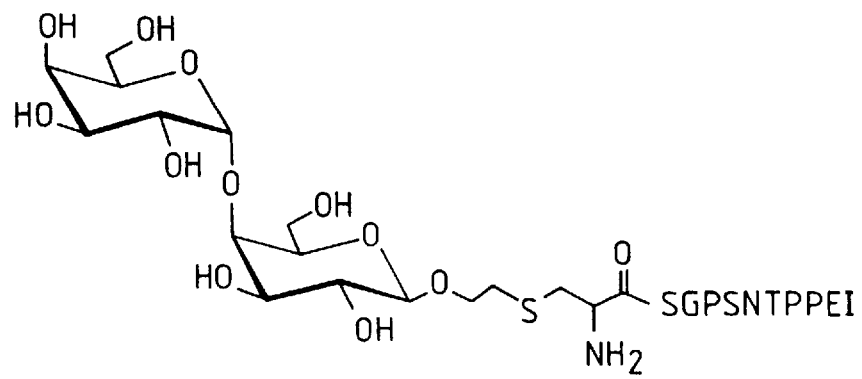
FIG. 9 Synthesis of glycopeptides (A and C). Glycopeptides were synthesised by coupling 2-bromoethyl 4-O-(α-D-galactopyranosyl)-β-D galactopyranoside (compound 28) with peptides containing a thiol function. A cysteine moiety was added to the native peptide sequence at the aminoterminus. Using cesium carbonate as a promoter, the nucleophilic property of the cysteine sulphur atom was utilised to create a thioether linkage between the peptide and the electrophilic spacer arm glycosidically linked to the carbohydrate moiety. The $Gal_2$ coupling reactions were performed in N,N-dimethylformamide. The coupling reactions were monitored by HPLC and were quenched by the addition of water containing 0.1% trifluoroacetic acid. The resulting glycopeptides (conjugates 29 (A) and 31 (C)) were purified by preparative HPLC and the molecular weights of the products were confirmed by FAB MS.
Figure 9B:
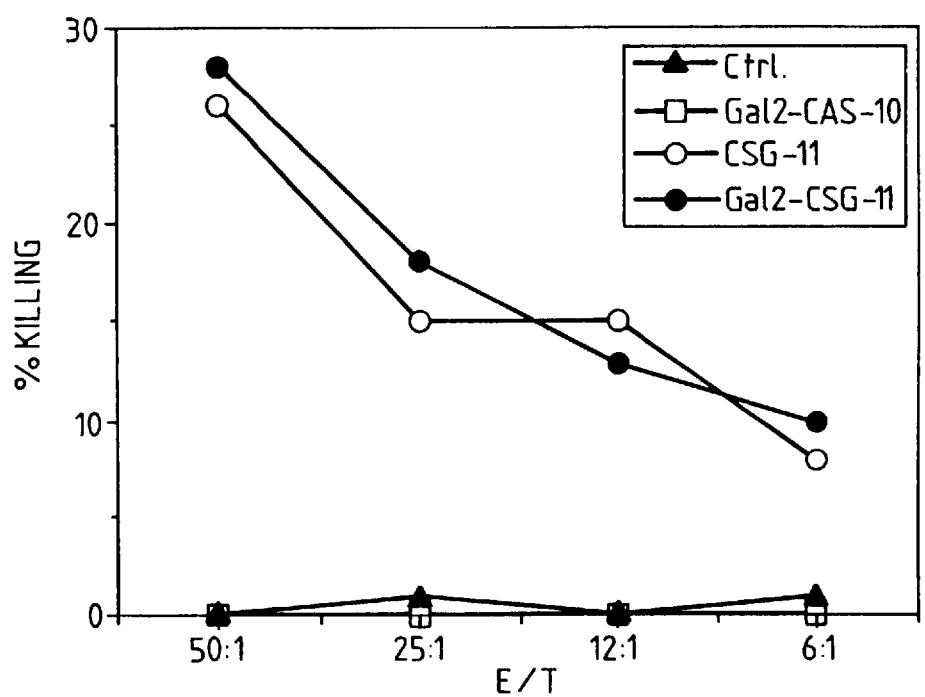
Figure 9C:
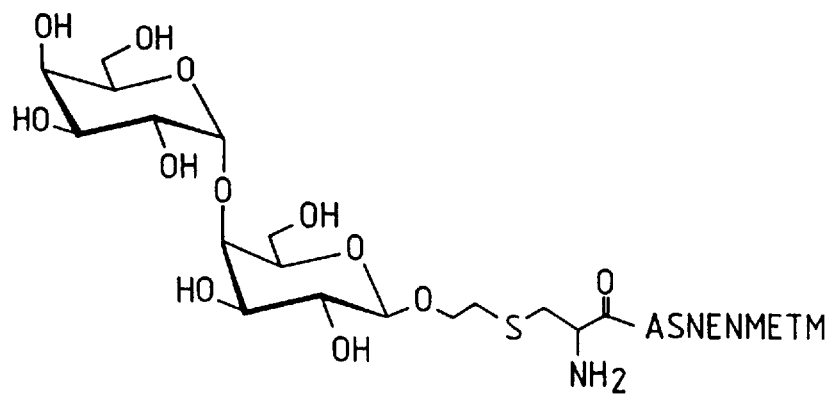
Figure 9D:
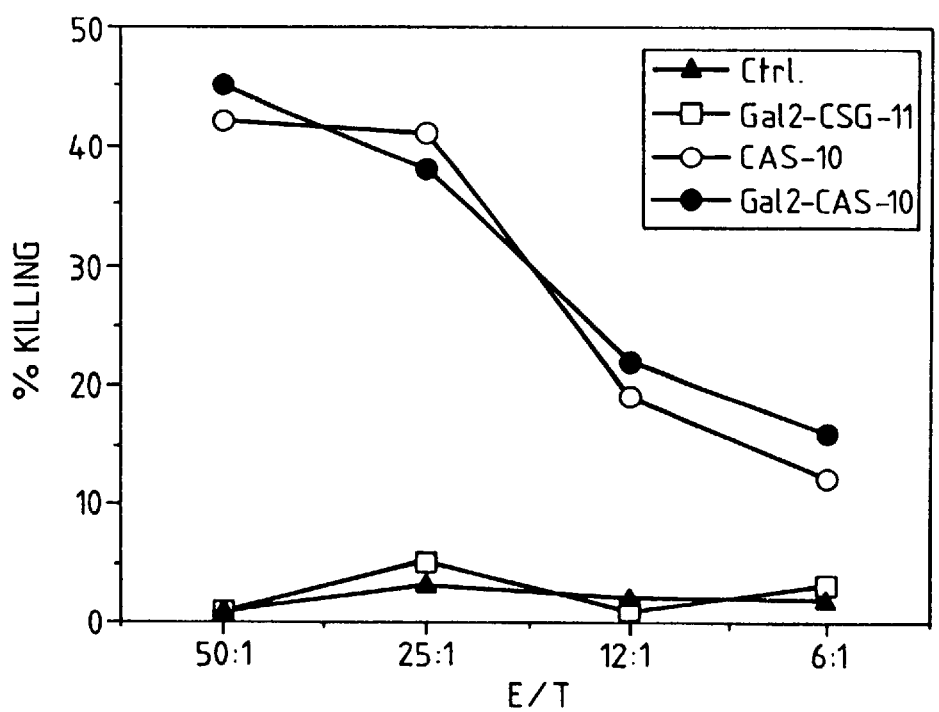
Figure 11A:
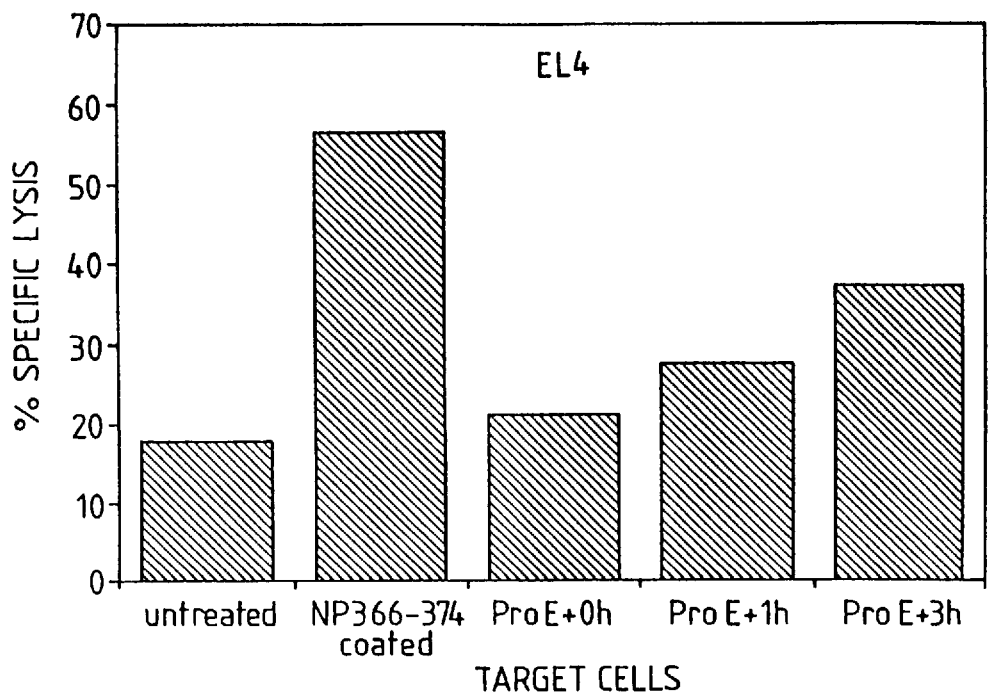
Figure 11B:
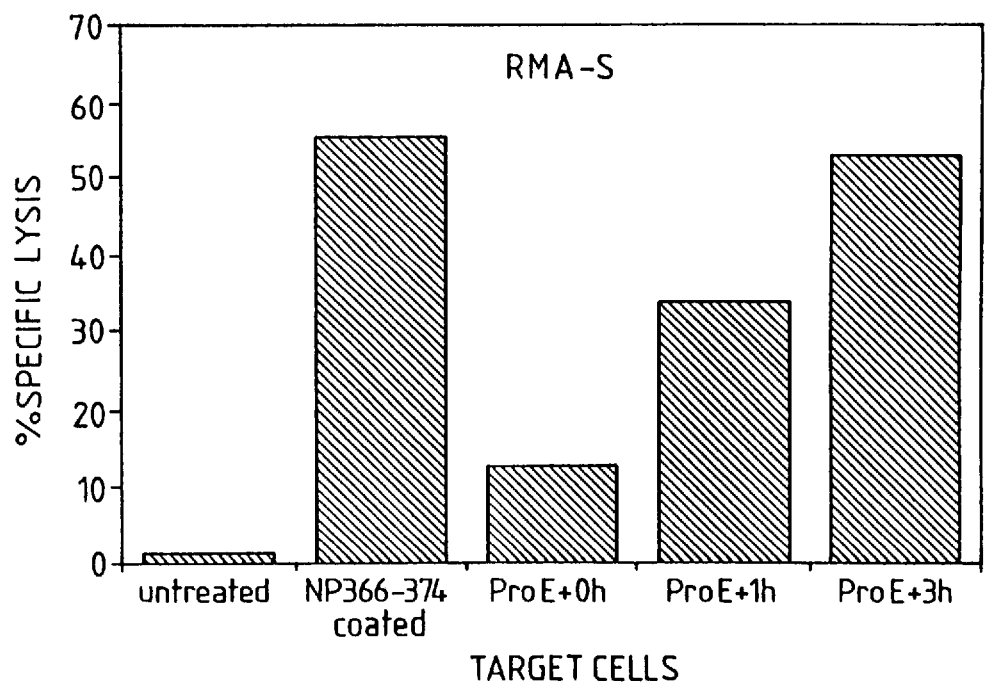

FIG. 11 Re-expression of $D^b$ bound peptide on EL4 (A) and RMA-S (B) cells after pronase treatment as detected by specific CTL. EL4 (A) and RMA-S (B) cells were treated with peptide NP366-374 (100 μM) for 1.5 hours. After washing, cells were treated with Pronase E (ProE, 4 mg/ml in RPMI 1640) washed, and cultured at 37° C. for 0, 1 and 3 hours and assayed in a 4 hour $^{51}$Cr release assay. CTL preparation has been previously described (Zhou et al., 1992 b). Briefly. C57B6/J female mice were immunized by one i.v. injection of 20 HAU of influenza A/PR/8/34 virus (a gift from Dr A. Douglas, National Institute for Medical Research, London) diluted in PBS. 1–4 weeks after the immunization, immune spleen cells were restimulated with irradiated, virus infected syngeneic spleen cells for 5 days.

Figure 12:
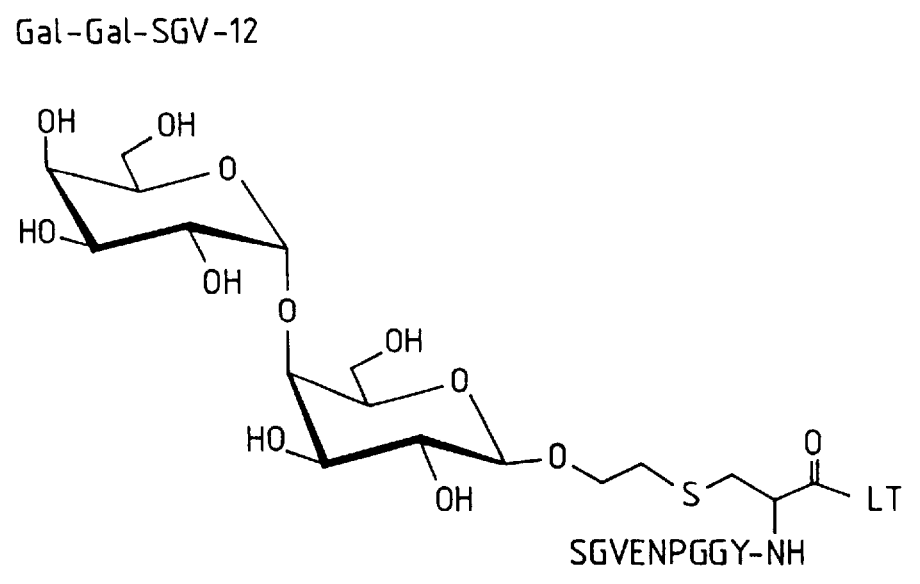

FIG. 12 The glycopeptide SGV12-$Gal_2$ (conjugate 30), used for generation of a carbohycirate-specific CTL response (cf. Example 4).

Figure 13A:
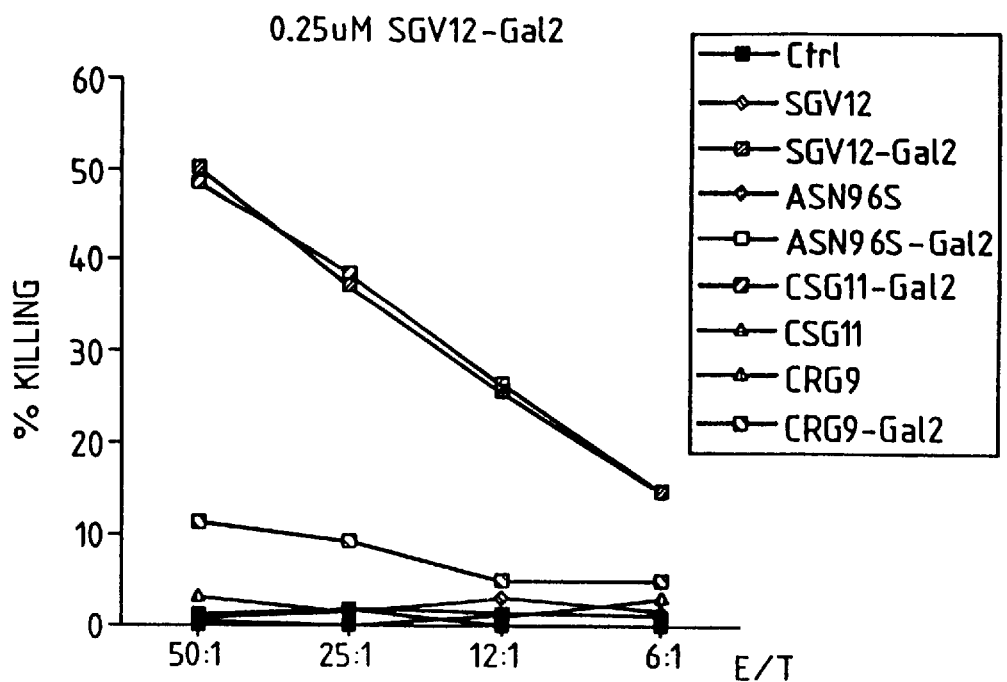
Figure 13B:
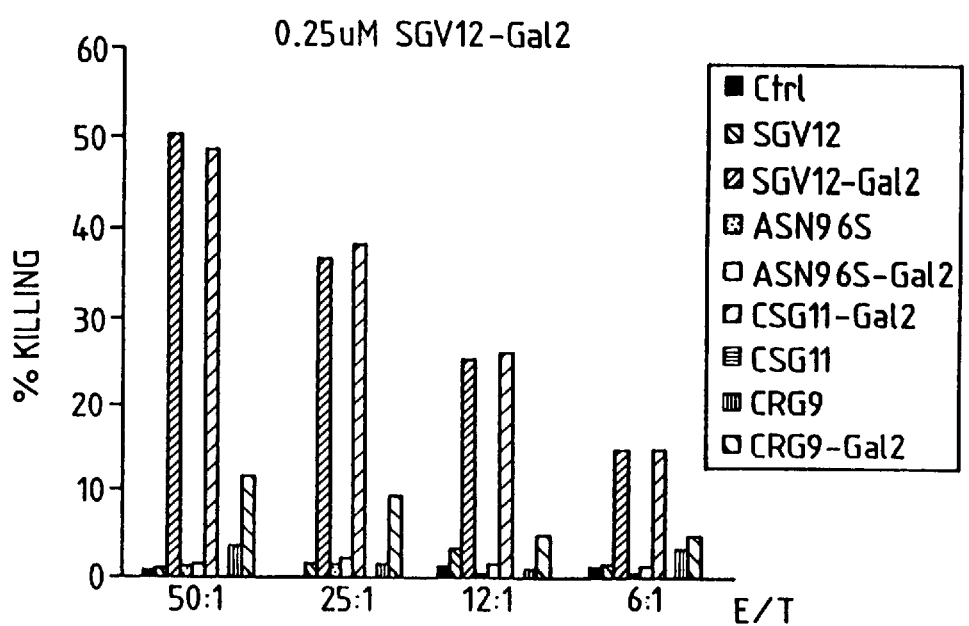

FIG. 13 SGV12-Gal2 generated CTL cells were tested against EL-4 cells coated with peptides/glycopeptides as indicated in the panel. E/T, Effector:target ratio.

Figure 14A:
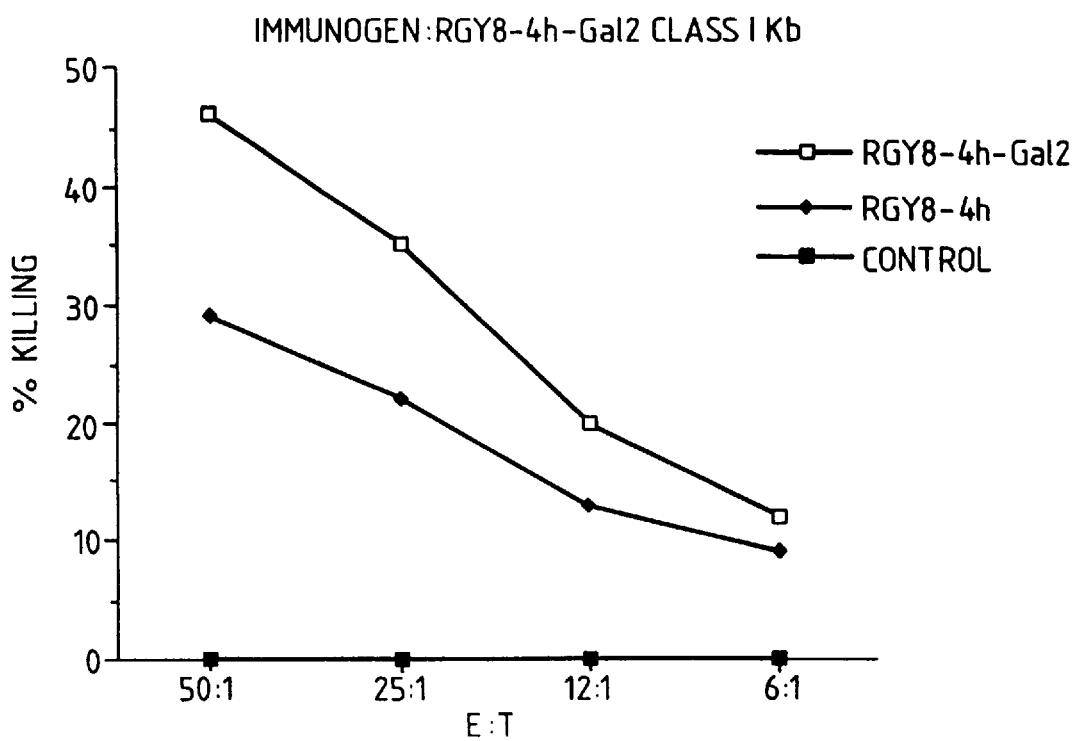
Figure 14B:
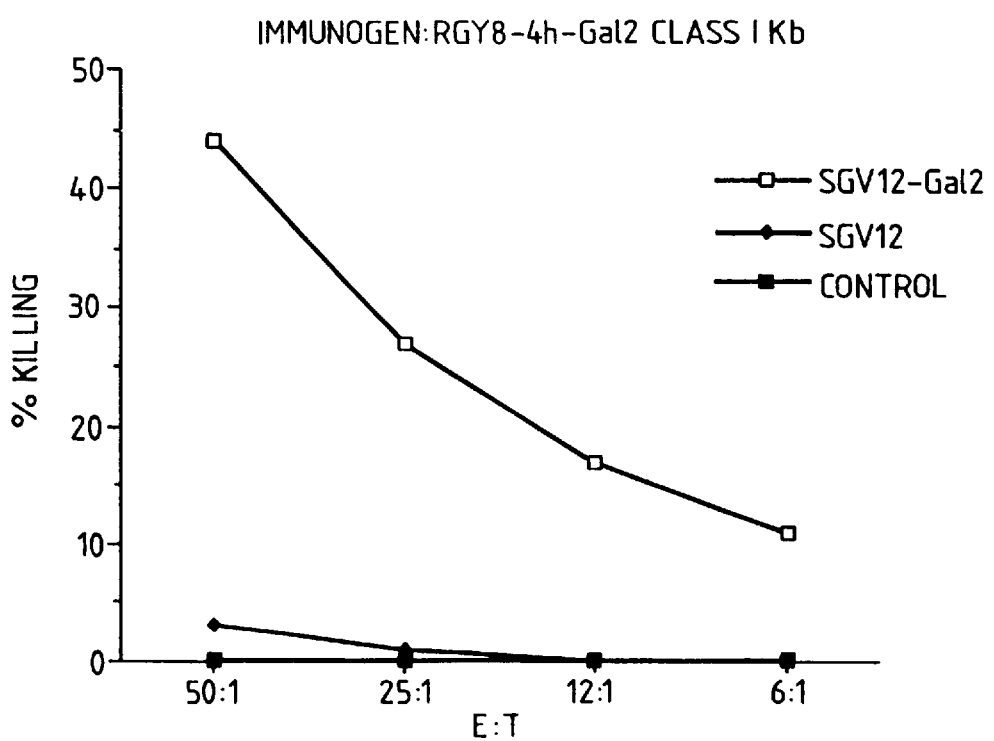

FIG. 14(A) and (B) RGY8–4h-$Gal_2$ generated CTL cells were tested against EL-4 cells coated with the indicated peptides/glycopeptides. E/T, Effector:target ratio.

REFERENCES

Alchele et al. (1990), J. Exp. Med. 171, 1815–1820.
Ansari, A. A., T. Frejd and G. Magnusson (1987), Carbohydr. Res. 161, 225–233.
Brodin et al (1988), Int. J. Cancer 42, 185–194.
Catelani, G. (1988), Carbohydr. Res. 182, 297–300.
Crowle (1988), Infect. Immun. 56, 2769–2773.
Dahmén et al. (1983 a), Carbohydrate Res. 113, 219–224.
Dahmén, J., T. Frejd, G. Gronberg, T. Lave, G. Magnusson and G. Noori (1983 b), Carbohydr. Res. 116, 303–307.
Dahmén, J. et al. (1984), Carbohydr. Res. 127,15–25.
Dasgupta, F. and P. J. Garegg (1988), Carbohydr. Res. 177, C13-C17.
Domer et aL (1989), Infect. Immun. 57, 693–700.
Elofsson, M., Walse, B. and Kihlberg, J. (1991), Tetrahedron Lett. 32, 7613–7616.
Falk et al. (1991), Nature 351, 290–296.
Fremont et al (1992), Science 257, 919–927.
Fung et al. (1990), Cancer Research 50, 4308–4314.
Hansen et al. (1990), J. Virol. 64, 2833–2844
Hakomori (1991), Current Opinion in Immunology 3, 646–653.
Harding (1992), Eur. J. Immunol. 22, 1865–1869.
Henningsson et al. (1987), Cancer Immunol. Immunother. 25, 231–241.
Hochman et al. (1991), J. Immunol. 146,1862–1867.
ishioka et al. (1992), J. Immunol. 148, 2446–2451.
Janeway (1991), Nature 353, 792.
Jansson, K., S. Ahifors, T. Frejd, J. Kihlberg and G. Magnusson (1988), J. Org. Chem. 53, 5629–5647.
Jardetzky et al. (1991), Nature 353, 326–329.
Jondal & Pross (1975), Int. J. Cancer 15, 596–605.
Jorgensen et al. (1992), Nature 355, 224–230.
Latron et al. (1992), Science 257, 964–967.
Lönn, H. and K. Stenvall (1992), Tetrahedron Lett. 33, 115–116.
Magnusson, G., S. Ahifors, J. Dahmén, K. Jansson, U. Nilsson, G. Noori, K. Stenvall and A. Tjörnebo (1982), J. Org. Chem. 55, 3932–3946.
Madden et al. (1991), Nature 353, 321–325.
Marra, A. and P. Sinaÿ (1990), Carbohydr. Res. 195, 303–308.
Marra, A. and P. Sinaÿ (1989), Carbohydr. Res. 187, 35–42.
Masazuni et al. (1992), Science 257, 927–934.
Moll et al. (1989), Infect. Immun. 57, 3349–3356
Morein et al. (1984), Nature 308, 457–460.
Murase, T., H. Ishida, M. Kiso and A. Hasegawa (1989), Carbohydr. Res. 188, 71–80.
Nores et al. (1987), J. Immunol. 139, 3171–3176.
Oettgen, H. F., Ed. (1989). Gangliosides and Cancer. pub. VCH.
Oldstone et al. (1988), J. Exp. Med. 168, 559–570.
Or, Y. S., Clark, R. F. & Luly, J. R. (1991) J. Org. Chem. 56, 3146–3149.

Ortmann et al. (1992), J. Immunol. 148, 1445–1450.
Otten et al. (1992), J. Immunol. 148, 3723–3732.
Portukalain et al. (1979), Eur. J. Biochem. 94, 19–23.
Ray, A. et al. (1992), J. Am. Chem. Soc. 114, 2256–2257.
Renaud, P. and D. Seebach (1986), Helv. Chim. Acta 69, 1704–1710.
Robertsson et al. (1982), Infect. Immun. 37, 737–748,
Rötzschke et al. (1990), Nature 348, 252–254.
Rötzschke & Falk (1991), Immunology Today 12, 447–455.
Sällberg et al. (1991), Immunol. Lett. 30, 59–68.
Stauss (1991), Current Biology 1, 328–330.
Thurin, Hackett, Otvos & Loibner, In Thurin: Abberant Glycosylation in Human Melanoma and Carcinoma (Doctorate in medical science, University of Gothenburg, 1991, ISBN-91-628-0389-1).
Townsend et al. (1985), Cell 42, 457–467.
Townsend et al. (1986), Cell 44, 959–968.
Tsomides & Eisen (1991) J. Biol. Chem. 266, 3357–3360.
Van Bleek & Nathenson (1990), Nature 348, 213–216.
Wiels et al. (1981) Proc. Natl. Acad. Sci. U.S.A. 78, 6485–6488.
Yang, C. C., Marlowe, C. K. & Kania, R. (1991) J. Am. Chem. Soc. 113, 3177–3178.
Zhou et al (1992 a), J. Immunol. Methods 153,193–200. (Published in August 1992.)
Zhou et al. (1992 b), Eur. J. Immunol. 22, 3085–3090. (Published in November 1992.)

I claim:

1. A peptide/carbohydrate conjugate which stimulates specific cytotoxic T cell immunity against a carbohydrate structure, said conjugate comprising (i) a peptide component capable of binding a MHC class I molecule; and (ii) a carbohydrate component having the immunogenic specificity of said carbohydrate structure.

2. The conjugate according to claim 1 which stimulates specific cytotoxic T cell immunity against a tumor-associated carbohydrate structure, said conjugate comprising (i) a peptide component capable of binding a MHC class I molecule; and (ii) a carbohydrate component having the immunogenic specificity of said tumor-associated carbohydrate structure.

3. The conjugate according to claim 1 which stimulates specific cytotoxic T cell immunity against a carbohydrate structure expressed on infectious agents or infected host cells, said conjugate comprising (i) a peptide component capable of binding a MHC class I molecule; and (ii) a carbohydrate component having the immunogenic specificity of said carbohydrate structure expressed on infectious agents and infected host cells.

4. The conjugate according to any one of claims 1–3 wherein the peptide component consists of 5–25 amino acids.

5. The conjugate according to claim 4 wherein the peptide component consists of 8–12 amino acids.

6. The conjugate according to claim 5 wherein the peptide component consists of 9 amino acids.

7. The conjugate according to claim 4 wherein the peptide component is capable of binding a human MHC class I molecule.

8. The conjugate according to claim 7 wherein the carbohydrate component is conjugated to the peptide component in a position to bind a hypervariable region of a T cell receptor.

9. The conjugate according to claim 8 wherein the carbohydrate component is sized to enable the T cell receptor to encompass an epitope of said carbohydrate structure.

10. A peptide-carbohydrate conjugate which stimulates specific cytotoxic T-cell immunity against a carbohydrate structure comprising a peptide component capable of binding an MHC class I molecule and a carbohydrate component selected from the group consisting of Galβ4GlcβCer, NeuAcα8NeuAcα3Galβ4GlcβCer (GD3), 9-0-Ac-GD3, NeuAcα8NeuAcα3 (GalNAcβ4)Galβ4GlcβCer (GD2), 9-0Ac-GD2, GalNAcα-Ser(Thr), NeuAcα6GalNAcα-Ser(Thr), Galβ3GlcNAc, NeuAcα3Galβ3(Fucα4)GlcNAcβ, NeuAcα3Galβ3(Fucα4)[NeuAcα6]GlcNAcβ, Galβ3(Fucα4)GlcNAcβGalβ3(Fucα4)GlcNAβ, NeuAcα3Galβ4(Fucα3)GlcNAβ, Galβ4(Fucα3)GlcNAcβ3Galβ4(Fucα3)GlcNAcβ (Dimer Lewis x), Galβ4(Fucα3)GlcNAcβ3Galβ4(Fucα3)GlcNAcβ3Galβ4(Fucα3)GlcNAcβ (Trimer Lewis x), NeuAcα3-Dimer Lewis x, NeuAcα3-trimer Lewis x, NeuAcα6-Oligomer Lewis x, Galβ4GlcNAcβ3Galβ4GlcNAcβ, Galβ3(Fucα4)GlcNAcβGalβGalβ4(Fucα3)GlcNAcβ, Fucα2Galβ3GalNAcβ4(NeuAcα3)Galβ4GlcβCer (Fuc-GM1), Galα4Galβ4GlcβCer (Gb3), Fucα2Galβ3GalNAcβ3Galα4Galβ4GlcβCer, NeuAcα3Galα3GalNAcβ3Galα4Galβ4GlcβCer, NeuAcα3Galβ4GlcβCer (GM3), mannan from *Candida albicans,* polysaccharide isolates from *Mycobacterium bovis* strain BCG, Lipophosphoglycan from *Leishmania major,* O-antigenic polysaccharides from *Salmonella typhimurium,* Fucα2galβ4(Fucα3)GlcNAcβ, GalNAcα3(Fucα2)Galβ3GlcNAcβ and lactonized forms of those carbohydrates above which contain sialic acid.

11. A pharmaceutical composition comprising a conjugate according to any one of claims 1–3 or 10 as active ingredient and a pharmaceutically acceptable carrier.

12. A process for producing a peptide/carbohydrate conjugate which stimulates specific cytotoxic T cell immunity against a carbohydrate structure which comprises the following procedure steps:

(a) selecting a peptide component capable of binding a MHC class I molecule, (b) selecting the desired carbohydrate component, conjugating the peptide and carbohydrate components such that the carbohydrate is bound at an internal position of the peptide, (d) screening for peptide/carbohydrate conjugates for the ability to induce carbohydrate specific cytotoxic T-cell immunity against the carbohydrate structure, and (e) recovering the peptide/carbohydrate conjugate.

\* \* \* \* \*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Ala  Ser  Asn  Glu  Asn  Met  Glu  Thr  Met
    1                       5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Ser  Gly  Pro  Ser  Asn  Thr  Pro  Pro  Glu  Ile
    1                       5                             10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly  Ile  Leu  Gly  Phe  Val  Phe  Thr  Leu
    1                       5

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Lys Ile Ala Ser Asn Glu Asn Met Asp Ala Met Glu Ser Ser Thr Leu
1               5                   1 0                  1 5

Glu Cys ( 2 ) INFORMATION FOR SEQ ID NO:5:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Lys Ile Ala Ser Asn Glu Asn Met Glu Thr Met Glu Cys
1               5                   1 0

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Lys Ala Ser Asn Glu Asn Met Glu Thr Met Cys
1               5                   1 0

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Cys Ala Ser Asn Glu Asn Met Glu Thr Met
1               5                   1 0

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Cys Ser Gly Pro Ser Asn Thr Pro Pro Glu Ile
1               5                   1 0

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Ser Gly Val Glu Asn Pro Gly Gly Tyr Cys Leu Thr
1               5                   10

(2) INFORMATION FOR SEQ ID NO:10:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (xi) SEQUENCE DESCRIPTION: SEQ ID NO:10:

Lys Gln Ile Ala Ser Asn Glu Asn Met Glu Thr Met Glu Ser Cys
1               5                   10                  15

(2) INFORMATION FOR SEQ ID NO:11:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (xi) SEQUENCE DESCRIPTION: SEQ ID NO:11:

Lys Gly Pro Ser Asn Thr Pro Pro Glu Ile Cys
1               5                   10

(2) INFORMATION FOR SEQ ID NO:12:

(i) SEQUENCE CHARACTERISTICS:
      (A) LENGTH: 13 amino acids
      (B) TYPE: amino acid
      (D) TOPOLOGY: linear (ii) MOLECULE TYPE: peptide (xi) SEQUENCE DESCRIPTION: SEQ ID NO:12:

Lys Ser Gly Pro Ser Asn Thr Pro Pro Glu Ile His Cys
1               5                   10

(2) INFORMATION FOR SEQ ID NO:13:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:13:

Cys Arg Gly Tyr Val Tyr Gln Gly Leu
1               5

(2) INFORMATION FOR SEQ ID NO:14:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:14:

Cys Ala Pro Gly Asn Tyr Pro Ala Leu
1               5

(2) INFORMATION FOR SEQ ID NO:15:

( i ) SEQUENCE CHARACTERISTICS:
  ( A ) LENGTH: 13 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:15:

```
Met  Val  Val  Lys  Leu  Gly  Glu  Phe  Tyr  Asn  Gln  Met  Met
1                 5                             10
```

( 2 ) INFORMATION FOR SEQ ID NO:16:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:16:

```
Cys  Pro  Thr  Asn  Gln  Gln  Val  Val  Leu  Glu  Gly  Thr  Asn  Lys  Thr  Asp
1                 5                             10                            15
```

( 2 ) INFORMATION FOR SEQ ID NO:17:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

```
Met  Gln  Ile  Arg  Gly  Phe  Val  Tyr  Phe  Val  Glu  Thr
1                 5                             10
```

( 2 ) INFORMATION FOR SEQ ID NO:18:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

```
Leu  Ser  Pro  Gly  Met  Met  Met  Gly  Met  Phe  Asn  Met
1                 5                             10
```

( 2 ) INFORMATION FOR SEQ ID NO:19:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

```
Asp  Tyr  Gly  Ile  Leu  Gln  Ile  Asn  Ser  Arg
1                 5                             10
```

( 2 ) INFORMATION FOR SEQ ID NO:20:

( i ) SEQUENCE CHARACTERISTICS:
    ( A ) LENGTH: 9 amino acids
    ( B ) TYPE: amino acid
    ( D ) TOPOLOGY: linear (i i) MOLECULE TYPE: peptide (x i) SEQUENCE DESCRIPTION: SEQ ID NO:20:

Phe Ala Pro Gly Asn Tyr Pro Ala Leu
1               5

(2) INFORMATION FOR SEQ ID NO:21:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 6..7
        (D) OTHER INFORMATION: /label=Xaa
            / note= "homocysteine"

(x i) SEQUENCE DESCRIPTION: SEQ ID NO:21:

Ala Ser Asn Glu Asn Xaa Glu Thr Met
1               5

(2) INFORMATION FOR SEQ ID NO:22:

(i) SEQUENCE CHARACTERISTICS:
        (A) LENGTH: 9 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 4..5
        (D) OTHER INFORMATION: /label=Xaa
            / note= "homocysteine"

(x i) SEQUENCE DESCRIPTION: SEQ ID NO:22:

Ala Ser Asn Xaa Asn Met Glu Thr Met
1               5

(2) INFORMATION FOR SEQ ID NO:23:

(i) SEQUENCE CHARACTERISTICS:
        (A) LENGTH: 10 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 6..7
        (D) OTHER INFORMATION: /label=Xaa
            / note= "homocysteine"

(x i) SEQUENCE DESCRIPTION: SEQ ID NO:23:

Ser Gly Pro Ser Asn Xaa Pro Pro Glu Ile
1               5                       10

(2) INFORMATION FOR SEQ ID NO:24:

(i) SEQUENCE CHARACTERISTICS:
        (A) LENGTH: 10 amino acids
        (B) TYPE: amino acid
        (D) TOPOLOGY: linear (i i) MOLECULE TYPE: peptide

```
( i x ) FEATURE:
        ( A ) NAME/KEY: Modified-site
        ( B ) LOCATION: 4..5
        ( D ) OTHER INFORMATION: /label=Xaa
                / note= "homocysteine"

( x i ) SEQUENCE DESCRIPTION: SEQ ID NO:24:

Ser  Gly  Pro  Xaa  Asn  Thr  Pro  Pro  Glu  Ile
1                   5                        10
```

( 2 ) INFORMATION FOR SEQ ID NO:25:

```
    ( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 4..5
            ( D ) OTHER INFORMATION: /label=Xaa
                    / note= "homocysteine"

( x i ) SEQUENCE DESCRIPTION: SEQ ID NO:25:

Arg  Gly  Tyr  Xaa  Tyr  Gln  Gly  Leu
    1                   5
```

( 2 ) INFORMATION FOR SEQ ID NO:26:

```
    ( i ) SEQUENCE CHARACTERISTICS:
            ( A ) LENGTH: 9 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 5..6
            ( D ) OTHER INFORMATION: /label=Xaa
                    / note= "homocysteine"

( x i ) SEQUENCE DESCRIPTION: SEQ ID NO:26:

Phe  Ala  Pro  Gly  Xaa  Tyr  Pro  Ala  Leu
    1                        5
```

( 2 ) INFORMATION FOR SEQ ID NO:27:

```
    ( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:27:

Arg  Gly  Tyr  Val  Tyr  Gln  Gly  Leu
    1                   5
```